US011723976B2

(12) United States Patent
Kameoka et al.

(10) Patent No.: US 11,723,976 B2
(45) Date of Patent: Aug. 15, 2023

(54) METHODS OF ADMINISTERING ANTI-IL31A ANTIBODY-CONTAINING FORMULATIONS

(71) Applicant: Chugai Seiyaku Kabushiki Kaisha, Tokyo (JP)

(72) Inventors: Daisuke Kameoka, Tokyo (JP); Toru Yoshizawa, Tokyo (JP); Megumi Numata, Tokyo (JP); Hitoshi Sasaki, Tokyo (JP); So Yamaguchi, Tokyo (JP); Hiroko Murata, Shizuoka (JP); Naoka Hironiwa, Singapore (SG)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 17 days.

(21) Appl. No.: 17/573,991

(22) Filed: Jan. 12, 2022

(65) Prior Publication Data
US 2022/0125921 A1    Apr. 28, 2022

Related U.S. Application Data

(60) Division of application No. 17/346,421, filed on Jun. 14, 2021, now Pat. No. 11,260,125, which is a continuation of application No. 17/058,399, filed as application No. PCT/JP2020/043125 on Nov. 19, 2020, now abandoned.

(30) Foreign Application Priority Data

Nov. 20, 2019    (JP) .................. 2019-209851

(51) Int. Cl.
| | | |
|---|---|---|
| C07K 16/28 | (2006.01) | |
| A61K 39/395 | (2006.01) | |
| A61K 47/10 | (2017.01) | |
| A61K 47/18 | (2017.01) | |
| A61K 47/26 | (2006.01) | |
| A61K 9/08 | (2006.01) | |
| A61K 9/19 | (2006.01) | |
| C07K 14/715 | (2006.01) | |
| A61K 39/00 | (2006.01) | |

(52) U.S. Cl.
CPC .......... *A61K 39/39591* (2013.01); *A61K 9/08* (2013.01); *A61K 9/19* (2013.01); *A61K 39/3955* (2013.01); *A61K 47/10* (2013.01); *A61K 47/18* (2013.01); *A61K 47/183* (2013.01); *A61K 47/26* (2013.01); *C07K 16/2866* (2013.01); *A61K 2039/505* (2013.01); *A61K 2039/54* (2013.01); *C07K 14/7155* (2013.01); *C07K 2317/56* (2013.01); *C07K 2317/565* (2013.01); *C07K 2317/76* (2013.01)

(58) Field of Classification Search
CPC ............ A61K 2039/505; A61K 39/395; A61K 39/3955; A61K 47/10; A61K 47/26; A61K 47/183; A61K 47/18; A61K 39/39591; A61K 2039/54; C07K 16/2866; C07K 14/7155; C07K 2317/56; C07K 2317/565; C07K 2317/76

See application file for complete search history.

(56) References Cited

U.S. PATENT DOCUMENTS

| | | |
|---|---|---|
| 5,455,030 A | 10/1995 | Ladner et al. |
| 6,018,032 A | 1/2000 | Koike et al. |
| 6,019,967 A | 2/2000 | Breton et al. |
| 6,887,852 B1 | 5/2005 | Paik et al. |
| 7,001,980 B1 | 2/2006 | Parker et al. |
| 7,064,186 B2 | 6/2006 | Sprecher et al. |
| 7,250,168 B2 | 7/2007 | Light et al. |
| 7,482,440 B2 | 1/2009 | Maeda et al. |
| 7,494,804 B2 | 2/2009 | Maeda et al. |
| 7,517,965 B2 | 4/2009 | Koga et al. |
| 7,575,938 B2 | 8/2009 | Chung et al. |
| 7,579,000 B2 | 8/2009 | Light et al. |

(Continued)

FOREIGN PATENT DOCUMENTS

| | | |
|---|---|---|
| AU | 2006214404 | 8/2006 |
| AU | 2007249713 | 11/2007 |

(Continued)

OTHER PUBLICATIONS

U.S. Appl. No. 16/713,271. filed Dec. 13, 2019, Kaneko et al.

(Continued)

*Primary Examiner* — Bridget E Bunner
(74) *Attorney, Agent, or Firm* — Fish & Richardson P.C.

(57) ABSTRACT

In one non-limiting embodiment, the present disclosure relates to lyophilized formulations containing an IL-31 antagonist (for example, an anti-IL-31RA antibody) as an active ingredient, the lyophilized formulations further containing arginine and/or a salt thereof and sucrose and/or trehalose. In another non-limiting embodiment, the present disclosure relates to solution formulations containing an IL-31 antagonist as an active ingredient, the solution formulations further containing arginine and/or a salt thereof. In other non-limiting embodiments, the present disclosure relates to methods for stabilizing an antibody (for example, an anti-IL-31RA antibody) in an antibody-containing formulation, methods for suppressing antibody aggregation (aggregate formation) in an antibody-containing formulation, and methods for reducing components with charge heterogeneity in an antibody-containing formulation, the methods being characterized in that the formulation is prepared to contain arginine and/or a salt thereof, and/or sucrose and/or trehalose.

30 Claims, No Drawings
Specification includes a Sequence Listing.

(56) References Cited

U.S. PATENT DOCUMENTS

| | | |
|---|---|---|
| 7,622,122 B2 | 11/2009 | Light et al. |
| 7,622,457 B2 | 11/2009 | Light et al. |
| 7,638,126 B2 | 12/2009 | Yao et al. |
| 7,858,756 B2 | 12/2010 | Owens et al. |
| 7,919,594 B2 | 4/2011 | Smith et al. |
| 8,075,884 B2 | 12/2011 | Bowdish et al. |
| 8,076,458 B2 | 12/2011 | Ohta et al. |
| 8,431,127 B2 | 4/2013 | Higuchi et al. |
| 8,575,317 B2 | 11/2013 | Kuramochi et al. |
| 9,028,821 B2 | 5/2015 | Hasegawa et al. |
| 9,198,898 B2 | 12/2015 | Zhang et al. |
| 9,399,680 B2 | 7/2016 | Kuramochi et al. |
| 9,745,378 B2 | 8/2017 | Hasegawa et al. |
| 10,544,227 B2 | 1/2020 | Kaneko et al. |
| 11,260,125 B2 | 3/2022 | Kameoka et al. |
| 2003/0096339 A1 | 5/2003 | Sprecher et al. |
| 2003/0215838 A1 | 11/2003 | Sprecher et al. |
| 2003/0224487 A1 | 12/2003 | Sprecher et al. |
| 2004/0142422 A1 | 7/2004 | Sprecher et al. |
| 2004/0223970 A1 | 11/2004 | Afar et al. |
| 2006/0121022 A1 | 6/2006 | Koga et al. |
| 2006/0182743 A1 | 8/2006 | Bilsborough |
| 2007/0160611 A1 | 7/2007 | Yao et al. |
| 2008/0125579 A1 | 5/2008 | Owens et al. |
| 2008/0219971 A1 | 9/2008 | Smith et al. |
| 2009/0028854 A1 | 1/2009 | Igawa et al. |
| 2009/0202556 A1 | 8/2009 | Ohta et al. |
| 2010/0055092 A1 | 3/2010 | Hasegawa et al. |
| 2010/0285030 A1 | 11/2010 | Bowdish et al. |
| 2010/0310556 A1 | 12/2010 | Higuchi et al. |
| 2011/0129459 A1 | 6/2011 | Kuramochi et al. |
| 2011/0229459 A1 | 9/2011 | Kuramochi et al. |
| 2014/0039165 A1 | 2/2014 | Kuramochi et al. |
| 2015/0057255 A1 | 2/2015 | Zhang et al. |
| 2015/0175704 A1 | 6/2015 | Kuramochi et al. |
| 2015/0315280 A1 | 11/2015 | Hasegawa et al. |
| 2018/0079817 A1 | 3/2018 | Kaneko et al. |
| 2020/0002429 A1 | 1/2020 | Kuramochi et al. |
| 2020/0102396 A1 | 4/2020 | Igawa et al. |
| 2021/0322550 A1 | 10/2021 | Kameoka et al. |
| 2022/0184210 A1 | 6/2022 | Kameoka et al. |

FOREIGN PATENT DOCUMENTS

| | | |
|---|---|---|
| AU | 2007255753 | 12/2007 |
| AU | 2008332271 | 6/2009 |
| BR | PI0821145-0 | 6/2015 |
| BR | PI0821110-8 | 7/2015 |
| CA | 2 272 245 | 5/1998 |
| CA | 2 589 670 | 6/2006 |
| CA | 2 594 490 | 8/2006 |
| CA | 2 633 439 | 11/2007 |
| CA | 2 636 288 | 12/2007 |
| CA | 2 708 065 | 6/2009 |
| CA | 2 708 532 | 6/2009 |
| CN | 1213070 | 8/2005 |
| CN | 1241944 | 2/2006 |
| CN | 1326880 | 7/2007 |
| CN | 100384876 | 4/2008 |
| CN | 101198624 | 6/2008 |
| CN | 100469793 | 3/2009 |
| CN | 101600456 | 12/2009 |
| CN | 101939424 | 1/2011 |
| EA | 009026 | 10/2007 |
| EP | 0 411 946 A | 2/1991 |
| EP | 0 931 646 A | 7/1999 |
| EP | 1 088 831 A | 4/2001 |
| EP | 1 188 830 A | 3/2002 |
| EP | 1 375 518 B | 10/2008 |
| EP | 2 047 863 A | 4/2009 |
| EP | 2 236 604 A | 10/2010 |
| EP | 2241 332 A | 10/2010 |
| EP | 2 354 161 A | 8/2011 |
| EP | 2 734 549 B | 5/2017 |
| EP | 3 284 480 A | 2/2018 |
| EP | 3 797 752 A | 3/2021 |
| JP | 2001-503781 | 3/2001 |
| JP | 2005-532045 | 10/2005 |
| JP | 2008-530138 | 8/2008 |
| JP | 2010-531340 | 9/2010 |
| JP | 2011-506302 | 3/2011 |
| JP | 5043008 | 10/2012 |
| JP | 2014-122220 | 7/2014 |
| KR | 10-2010-0097721 | 9/2010 |
| KR | 10-2021-0010996 | 1/2021 |
| RU | 2180854 | 3/2002 |
| RU | 2010/127292 | 1/2012 |
| RU | 2010/126078 | 1/2013 |
| RU | 2511406 | 4/2014 |
| RU | 2749512 | 6/2021 |
| TW | 2008/10778 | 3/2008 |
| TW | 2009/32266 | 8/2009 |
| TW | 2010/28165 | 8/2010 |
| WO | WO 94/10354 | 5/1994 |
| WO | WO 94/12215 | 6/1994 |
| WO | WO 96/23071 | 8/1996 |
| WO | WO 97/10354 | 3/1997 |
| WO | WO 99/55735 | 11/1999 |
| WO | WO 00/34317 | 6/2000 |
| WO | WO 00/75314 | 12/2000 |
| WO | WO 01/23556 | 4/2001 |
| WO | WO 02/00721 | 1/2002 |
| WO | WO 02/77230 | 10/2002 |
| WO | WO 03/060090 | 7/2003 |
| WO | WO 03/072740 | 9/2003 |
| WO | WO 2004/003140 | 1/2004 |
| WO | WO 2004/085476 | 10/2004 |
| WO | WO 2004/091543 | 10/2004 |
| WO | WO 2005/079566 | 9/2005 |
| WO | WO 2006/004663 | 1/2006 |
| WO | WO 2006/063864 | 6/2006 |
| WO | WO 2006/063865 | 6/2006 |
| WO | WO 2006/070286 | 7/2006 |
| WO | WO 2006/081573 | 8/2006 |
| WO | WO 2006/088855 | 8/2006 |
| WO | WO 2006/088955 | 8/2006 |
| WO | WO 2006/088956 | 8/2006 |
| WO | WO 2006/118959 | 11/2006 |
| WO | WO 2006/119062 | 11/2006 |
| WO | WO 2006/122079 | 11/2006 |
| WO | WO 2007/108756 | 9/2007 |
| WO | WO 2007/133816 | 11/2007 |
| WO | WO 2007/142325 | 12/2007 |
| WO | WO 2007/143231 | 12/2007 |
| WO | WO 2008/028192 | 3/2008 |
| WO | WO 2008/073463 | 6/2008 |
| WO | WO 2008/103432 | 8/2008 |
| WO | WO 2008/132453 | 11/2008 |
| WO | WO 2009/007272 | 1/2009 |
| WO | WO 2009/041613 | 4/2009 |
| WO | WO 2009/041621 | 4/2009 |
| WO | WO 2009/041643 | 4/2009 |
| WO | WO 2009/071696 | 6/2009 |
| WO | WO 2009/072598 | 6/2009 |
| WO | WO 2009/072604 | 6/2009 |
| WO | WO 2010/064456 | 6/2010 |
| WO | WO 2010/064697 | 6/2010 |
| WO | WO 2010/148253 | 12/2010 |
| WO | WO 2013/012022 | 1/2013 |
| WO | WO 2014/208645 | 12/2014 |
| WO | WO 2016/167263 | 10/2016 |
| WO | WO 2018/154319 | 8/2018 |
| WO | WO 2018/156367 | 8/2018 |
| WO | WO 2018/191414 | 10/2018 |
| WO | WO 2019/225568 | 11/2019 |
| WO | WO 2021/100794 | 5/2021 |

OTHER PUBLICATIONS

U.S. Appl. No. 16/988,554, filed Aug. 7, 2020, Kerrouche et al.
U.S. Appl. No. 17/058,399, filed Nov. 24, 2020, Kameoka et al.
Arakawa et al., "The Effects of Protein Stabilizers on Aggregation Induced by Multiple-Stresses," Yakugaku Zasshi, Nov. 2003,

(56) References Cited

OTHER PUBLICATIONS

123(11):957-961. doi: 10.1248/yakushi.123.957. PMID: 1463175 (with English translation).
Beiboer et al., "Guided Selection of a Pan Carcinoma Specific Antibody Reveals Similar Binding Characteristics yet Structural Divergence Between the Original Murine Antibody and its Human Equivalent," J Mol Biol, Feb. 25, 2000, 296(3):833-849.
Bendig, "Humanization of rodent monoclonal antibodies by CDR grafting," Methods: A Comparison to Methods in Enzymology, 1995, 8:83-93.
Benjamini et al., "Antigenicity," Immunology: A Short Course, $2^{nd}$ ed., 1991, p. 40.
Berglund et al., "The epitope space of the human proteome," Protein Sci, Apr. 2008, 17(4):606-613, doi: 10.1110/ps.073347208.
Bilsborough, "IL-31 is associated with cutaneous lymphocyte antigen-positive skin homing T cells in patients with atopic dermatitis," J Allergy Clin Immunol, Feb. 2006, 117(2):418-425.
Burgess et al., "Possible dissociation of the heparin-binding and mitogenic activities of heparin-binding (acidic fibroblast) growth factor-1 from its receptor-binding activities by site-directed mutagenesis of a single lysine residue," J Cell Biol, Nov. 1990, 111:2129-2138.
Carpenter et al., "Rational Design of Stable Lyophilized Protein Formulations: Some Practical Advice," PharmRes, Aug. 1997, 14(8):969-975.
Casset et al., "A peptide mimetic of an anti-CD4 monoclonal antibody by rational design," Biochem Biophys Res Commun, Jul. 18, 2003, 307:198-205.
Castellani et al., "Interleukin-31: A New Cytokine Involved in Inflammation of the Skin," Int J Immunopathol Pharmacol, Jan.-Mar. 2006, 19:1-4.
Chattopadhyay et al., "Interleukin-31 and Oncostatin-M Mediate Distinct Signaling Reactions and Response Patterns in Lung Epithelial Cells," J Biol Chem, Feb. 2, 2007, 282(5):3014-3026. doi: 10.1074/jbc.M609655200.
Chen et al., "Selection and analysis of an optimized anti-VEGF antibody: crystal structure of an affinity-matured Fab in complex with antigen," J Mol Biol, Nov. 5, 1999, 293(4):865-881.
Chirino et al., "Minimizing the immunogenicity of protein therapeutics," Drug Discov Today, Jan. 5, 2004, 9(2):82-90.
Costantino et al., "Effect of excipients on the stability and structure of lyophilized recombinant human growth hormone," J Pharm Sci, Nov. 1998, 87(11):1412-1420. doi: 10.1021/js980069t. PMID: 9811499.
Cork et al., "Epidermal barrier dysfunction in atopic dermatitis," J Invest Dermatol, Aug. 2009, 129(8):1892-1908.
De Pascalis et al., "Grafting of 'abbreviated' complementarity-determining regions containing specificity-determining residues essential for ligand contact to engineer a less immunogenic humanized monoclonal antibody," J Immunol, Sep. 15, 2002, 169(6):3076-3084.
Dillon et al., "Interleukin 31, a cytokine produced by activated T cells, induces dermatitis in mice," Nat Immunol, Jul. 2004, 5(7):752-760, Epub Jun. 6, 2004.
Dillon et al., "Transgenic Mice Overexpressing a Novel Cytokine (IL-31) Develop a Severe Pruritic Skin Phenotype Resembling Atopic Dermatitis," Eur Cytokine Netw, 2003, 14(suppl. 3):81 (#223).
Diveu et al., "Predominant expression of the long isoform of the GP130-like (GPL) receptor is required for interleukin-31 signaling," Eur Cytokine Netw, Oct.-Dec. 2004, 15:291-302.
Diveu et al., "GPL, a novel cytokine receptor related to GP130 and leukemia inhibitory factor receptor," J Biol Chem, Dec. 12, 2003, 278(50):49850-49859.
Ewert et al., "Stability improvement of antibodies for extracellular and intracellular applications: CDR grafting to stable frameworks and structure-based framework engineering," Methods, Oct. 2004, 34:184-199.
Fukuda et al., "Thermodynamic and fluorescence analyses to determine mechanisms of IgG1 stabilization and destabilization by arginine," Pharm Res, Apr. 2014, 31(4):992-1001.

Gershoni et al., "Epitope Mapping," BioDrugs, May 2007, 21(3):145-156.
Ghilardi et al., "A novel type I cytokine receptor is expressed on monocytes, signals proliferation, and activates STAT-3 and STAT-5," J Biol Chem, May 10, 2002, 27(19):16831-16836. Epub Mar. 4, 2002.
Grimstad et al., "Anti-interleukin-31-antibodies ameliorate scratching behaviour in NC/Nga mice: a model of atopic dermatitis," Exp Dermatol, Jan. 2009, 18(1):35-43.
Hanes et al., "Picomolar affinity antibodies from a fully synthetic naive library selected and evolved by ribosome display," Nat Biotechnol, Dec. 2000, 18(12):1287-1292.
Higa et al., "Administration of anti-interleukin 18 antibody fails to inhibit development of dermatitis in atopic dermatitis-model mice NC/Nga," Br J Dermatol, Jul. 2003, 149:39-45.
History of Changes for Study: NCT01614756: A Two-Part, Phase 1, Single-Dose Study of IL-31 mAb (Anti-Interleukin 31 Monoclonal Antibody) in Healthy Subjects and Adults With Atopic Dermatitis, Submitted Date: Feb. 19, 2015 (v13).
Holm et al., "Functional mapping and single chain construction of the anti-cytokeratin 8 monoclonal antibody TS1," Mol Immunol, Feb. 2007, 44(6):1075-1084, Epub Sep. 20, 2006.
Hudson et al., "Recombinant antibody fragments," Current Opinion in Biotechnology, Aug. 31, 1998, 9(4):395-402.
Kabashima et al., "Nemolizumab in patients with moderate-to-severe atopic dermatitis: Randomized, phase II, long-term extension study," J Allergy Clin Immunol, Oct. 2018, 142(4):1121-1130.e7.
Kasutani et al., "Anti-IL-31 receptor antibody is shown to be a potential therapeutic option for treating itch and dermatitis in mice," Br J Pharmacol, Nov. 2014, 171(22):5049-5058.
Klimka et al., "Human anti-CD30 recombinant antibodies by guided phage antibody selection using cell panning," Br J Cancer, Jul. 2000, 83(2):252-260.
Kim et al., "Arginine as a protein stabilizer and destabilizer in liquid formulations," Int J Pharm, Nov. 20, 2016, 513(1-2):26-37.
Kim et al., "IL-31 Serum Protein and Tissue mRNA Levels in Patients with Atopic Dermatitis," Ann Dermatol, Nov. 2011, 23(4):468-473, doi: 10.5021/ad.2011.23.4.468. Epub Nov. 3, 2011.
Krauss et al., "Impact of antibody framework residue VH-71 on the stability of a humanised anti-MUC1 scFv and derived immunoenzyme," Br J Cancer, May 4, 2004, 90:1863-1870.
Lazar et al., "Transforming growth factor alpha: mutation of aspartic acid 47 and leucine 48 results in different biological activities," Mol Cell Biol, Mar. 1988, 8:1247-1252.
Levin et al., "Optimizing the affinity and specificity of proteins with molecular display," Mol Biosyst, Jan. 2006, 2(1):49-57. Epub Nov. 8, 2005.
MacCallum et al., "Antibody-antigen interactions: contact analysis and binding site topography," J Mol Biol, Oct. 11, 1996, 262:732-745.
Macneal, Robert J., "Itching (Pruritus)," Merck Manual, May 2009, retrieved from the Internet on Jun. 10, 2011, http://www.merckmanuals.com/professional/sec10/ch109/ch109d.html, 6 pages.
Marks et al., "By-passing immunization: building high affinity human antibodies by chain shuffling," Biotechnology NY, Jul. 1992, 10(7):779-783.
Moiseenko, "Monoclonal Antibodies in the Treatment of Malignant Tumors," Practical Oncology, 2003, 4(3):148-156 (with what are believed to be the corresponding pages from an English version of Practical Oncology).
Montes-Torres et al., "Biological Treatments in Atopic Dermatitis," J Clin Med, Apr. 3, 2015, 4(4):593-613, doi: 10.3390/jcm4040593.
Monti et al., "Sleep and nighttime pruritus in children with atopic dermatitis," Sleep, Aug. 1989, 12(4):309-314.
Nagata et al., "Novel IL-31 cytokine," Rheumatology, 2006, 35:282-286.
Nemoto et al., "Phase I Trial of IL-31 Receptor Antibody $CIM_{331}$ in Healthy Adult Males and Atopic Dermatitis Patients," Nihon Hihuka Gakkai Zasshi, 2014, 124(4):779 (p. 7-5), 2 pages (with English translation).
Nemoto et al., "Phase I Trial of IL-31 Receptor Antibody CIM331 in Healthy Adult Males and Atopic Dermatitis Patients," Poster

(56) References Cited

OTHER PUBLICATIONS session of the 113th Annual Meeting of the Japanese Dermatological Association, May 30, 2014, 9 pages (with English translation).
Nemoto et al., "The first trial of $CIM_{331}$, a humanized antihuman interleukin-31 receptor A antibody, in healthy volunteers and patients with atopic dermatitis to evaluate safety, tolerability and pharmacokinetics of a single dose in a randomized, double-blind, placebo-controlled study," Br J Dermatol, Feb. 2016, 174(2):296-304, doi: 10.1111/bjd.14207. Epub Dec. 19, 2015.
Neis et al., "Enhanced expression levels of IL-31 correlate with IL-4 and IL-13 in atopic and allergic contact dermatitis," J Allergy Clin Immunol, Oct. 2006, 118(4):930-937, Epub Sep. 1, 2006.
Ohno et al., "Antigen-binding specificities of antibodies are primarily determined by seven residues of $V_H$," Proc Natl Acad Sci USA, May 1985, 82(9):2945-2949.
Onda et al., "Lowering the isoelectric point of the Fv portion of recombinant immuno toxins leads to decreased nonspecific animal toxicity without affecting antitumor activity," Cancer Res, Jul. 1, 2001, 61(13):5070-5077.
Padlan et al., "Identification of specificity-determining residues in antibodies," FASEB J, 1995, 9:133-139.
Padlan et al., "X-ray crystallography of antibodies," Adv Protein Chem, 1996, 49:57-133.
Pakula et al., "Genetic Analysis of Protein Stability and Function," Annu Rev Genet, 1989, 23:289-310.
Paul, "Structure and function of immunoglobulins," Fundamental Immunology, $3^{rd}$ ed., 1993, pp. 292-295.
Kuester et al., Chapter 3 "Pharmacokinetics of Monoclonal Antibodies," Pharmacokinetics and Pharmacodynamics of Biotech Drugs: Principles and Case-Studies in Drug Development, Ed. Bernd Meibohm, Wiley-VCH Verlag GmbH & Co. KGaA, 2006, pp. 45-91.
Phillips, "The challenge of gene therapy andDNA delivery," J Pharm Pharmacol, Sep. 2001, 53:1169-1174.
Pirollo et al., "Targeted delivery of small interfering RNA: approaching effective cancer therapies," Cancer Res, Mar. 1, 2008, 68:1247-1250.
R&D Systems, "Anti-human IL-31 RA Antibody," Catalog #AF2769, Oct. 2008, 1 page.
R&D Systems, "Biotinylated Anti-human IL-31 RA Antibody," Catalog #BAF2769, Nov. 2005, 1 page.
Raap et al., "Correlation of IL-31 serum levels with severity of atopic dermatitis," J Allergy Clin Immunol, Aug. 2008, 122(2):421-423 doi: 10.1016/j.jaci. 2008,05,047.
Rader et al., "A phage display approach for rapid antibody humanization: designed combinatorial V gene libraries," Proc Natl Acad Sci USA, Jul. 21, 1998, 95(15):8910-8915.
"Randomized, double-blind, placebo-controlled, multi-center, multi-dose Phase II study of anti-interleukin-31 receptor A monoclonal antibody CIM331 (nemolizumab) in patients with moderate-to-severe atopic dermatitis," 74th Annu Meet Am Acad Dermatol (AAD), Mar. 4-8, 2016 (Abst F053).
Roitt et al., Immunology, M., Mir, 2000, pp. 110, 150, and 537-539 (with what are believed to be the corresponding pages from an English version of Immunology).
Roitt et al., Immunology, M., Mir, 2000, pp. 110-111 (with what are believed to be the corresponding pages from an English version of Immunology).
Rose-John et al., "Interleukin-6 biology is coordinated by membrane-bound and soluble receptors: role in inflammation and cancer," J Leukoc Biol, Aug. 2006, 80(2):227-236, Epub May 17, 2006.
Rudikoff et al., "Single amino acid substitution altering antigen-binding specificity," Proc Natl Acad Sci USA, Mar. 1982, 79(6):1979-1983.
Ruzicka et al., "Anti-Interleukin-31 Receptor A Antibody for Atopic Dermatitis," N Engl J Med, Mar. 2, 2017, 376(9):826-835. doi: 10.1056/NEJMoa1606490.
"Safety and tolerability of a humanized monoclonal antibody to the Interleukin-31 receptor; results of a phase I, single ascending dose study, in healthy volunteers and patients with atopic dermatitis," Abst FC03.9, 22nd Congr Eur Acad Dermatol Venereol (EADV), Oct. 3-6, 2013.
Sato et al., "Reshaping a human antibody to inhibit the interleukin 6-dependent tumor cell growth," Cancer Res, Feb. 15, 1993, 53:851-856.
Singer et al., Genes & Genomes, 1998, 1:63 (with English translation).
Sonkoly et al., "IL-31: a new link between T cells and pruritus in atopic skin inflammation," J Allergy Clin Immunol, Feb. 2006, 117:411-417.
Takaoka et al., "Expression of IL-31 gene transcripts in NC/Nga mice with atopic dermatitis," Eur J Pharmacol, Jun. 1, 2005, 516(2):180-181.
Tan et al., "Engineering the isoelectric point of a renal cell carcinoma targeting antibody greatly enhances scFv solubility," Immunotechnology, Oct. 1998, 4(2):107-114.
Vajdos et al., "Comprehensive functional maps of the antigen-binding site of an anti-ErbB2 antibody obtained with shotgun scanning mutagenesis," J Mol Biol, Jul. 5, 2002, 320(2):415-428.
Vidal et al., "Making sense of antisense," Eur J Cancer, Dec. 2005, 41:2812-2818.
Wang et al., "Lyophilization and development of solid protein pharmaceuticals," Int J Pharmaceutics, 2000, 203, pp. 1-60.
Wang et al., "Antibody structure, instability, and formulation," J Pharmaceutical Sci, 2007, 96(1):1-26.
Yagi et al., "Interleukin-31 stimulates production of inflammatory mediators from human colonic subepithelial myofibroblasts," Int J Mol Med, Jun. 2007, 19(6):941-946.
Yamaguchi et al., "Characterization of itch-associated responses of NC mice with mite-induced chronic dermatitis," J Dermatol Sci, Jan. 2001, 25(1):20-28.
Yang et al., "CDR walking mutagenesis for the affinity maturation of a potent human anti-HIV-1 antibody into the picomolar range," J Mol Biol, Dec. 1, 1995, 254(3):392-403.
Zhang et al., "Structures and biological functions of IL-31 and IL-31 receptors," Cytokine Growth Factor Rev, Oct.-Dec. 2008, 19:347-356. Epub Oct. 15, 2008.
USPTO Restriction Requirement in U.S. Appl. No. 12/303,684, dated Aug. 23, 2010, 7 pages.
USPTO Non-Final Office Action in U.S. Appl. No. 12/303,684, dated Oct. 14, 2010, 18 pages.
USPTO Restriction Requirement in U.S. Appl. No. 12/303,684, dated Jun. 21, 2011, 5 pages.
USPTO Final Office Action in U.S. Appl. No. 12/303,684, dated Oct. 14, 2011, 17 pages.
USPTO Non-Final Office Action in U.S. Appl. No. 12/303,684, dated Aug. 26, 2014, 10 pages.
USPTO Non-Final Office Action in U.S. Appl. No. 12/746,229, dated Jun. 16, 2011, 16 pages.
USPTO Restriction Requirement in U.S. Appl. No. 12/746,229, dated Apr. 12, 2012, 5 pages.
USPTO Restriction Requirement in U.S. Appl. No. 12/746,229, dated Jun. 25, 2012, 4 pages.
U.S. Appl. No. 17/346,421, filed Jun. 14, 2021, Kameoka et al.
U.S. Appl. No. 17/686,536, filed Mar. 4, 2022, Kameoka et al.
USPTO Restriction Requirement in U.S. Appl. No. 12/809,138, dated Dec. 13, 2012, 8 pages.
USPTO Notice of Allowance in U.S. Appl. No. 17/346,421, dated Nov. 18, 2021, 15 pages.
Fish & Richardson P.C., Reply to Notice of Allowance in U.S. Appl. No. 17/346,421, filed Jan. 18, 2022, 4 pages.
U.S. Appl. No. 17/975,865, filed Oct. 28, 2022, Kuramochi et al.
U.S. Appl. No. 12/745,781, Kuramochi et al., filed Sep. 13, 2010 (abandoned).
U.S. Appl. No. 14/340,883, Kuramochi et al., filed Jul. 25, 2014 (abandoned).
U.S. Appl. No. 16/560,143, Kuramochi et al., filed Sep. 4, 2019.
International Preliminary Report on Patentability and Written Opinion in International Application No. PCT/JP2020/043125, dated Jun. 2, 2022, 6 pages.
U.S. Appl. No. 17/975,865, Kuramochi et al., filed Oct. 28, 2022.

METHODS OF ADMINISTERING ANTI-IL31A ANTIBODY-CONTAINING FORMULATIONS

CROSS-REFERENCE TO RELATED APPLICATIONS

This application is a divisional application of U.S. application Ser. No. 17/346,421, filed on Jun. 14, 2021, which is a continuation application of U.S. application Ser. No. 17/058,399, filed on Nov. 24, 2020 (now abandoned), which is the National Stage of International Application No. PCT/JP2020/043125, filed on Nov. 19, 2020, which claims the benefit of Japanese Application No. 2019-209851, filed on Nov. 20, 2019. The contents of the applications referenced above are incorporated herein by reference in their entireties.

SEQUENCE LISTING

This application contains a Sequence Listing that has been submitted electronically as an ASCII text file named SequenceListing.txt. The ASCII text file, created on Dec. 10, 2021, is 18.8 kilobytes in size. The material in the ASCII text file is hereby incorporated by reference in its entirety.

TECHNICAL FIELD

The present invention relates to stable formulations comprising an interleukin-31 (IL-31) antagonist (for example, a monoclonal antibody having the function to bind to IL-31 receptor A (IL-31RA) and to inhibit binding of IL-31 to IL-31RA).

BACKGROUND ART

Monoclonal antibodies having the function to bind to interleukin-31 (IL-31) receptor A (IL-31RA) and to inhibit binding of IL-31 to IL-31RA were identified (PTLs 1-3). Anti-IL-31RA antibody Nemolizumab (CIM331) is a humanized IgG2 antibody which acts as an IL-31 antagonist to inhibit functions of IL-31 which is known as a pruritus-inducing cytokine; therefore, clinical trials on atopic dermatitis patients are currently ongoing.

Aiming to improve stability, numerous lyophilized formulations for therapeutic proteins such as antibodies have been developed so far (NPL 1). As additives for lyophilized formulations for non-antibody therapeutic proteins, sugars such as sucrose and trehalose are commonly used (NPL 2), and there are reports of cases where arginine was used as a stabilizing agent (PTLs 4 and 5).

However, for a formulation comprising an anti-IL31RA antibody (CIM331) which is an IL-31 antagonist, there is no report on a stable formulation where aggregate formation and/or components with charge heterogeneity which largely affects the antibody stability is suppressed.

CITATION LIST

Patent Literature

[PTL 1] WO2007/142325
[PTL 2] WO2009/072604
[PTL 3] WO2010/064697
[PTL 4] U.S. Pat. No. 6,887,852B1
[PTL 5] WO2010/148253

Non-Patent Literature

[NPL 1] Pharm Res. 1997; 14(8): 969-975.
[NPL 2] J Pharm Sci. 1998; 87(11): 1412-1420.

SUMMARY OF THE INVENTION

Technical Problem

An objective of the present invention is to provide stable formulations that comprise an anti-IL-31RA antibody (CIM331) which is an IL-31 antagonist as an active ingredient.

Solution to Problem

The present inventors have conducted dedicated research to achieve the above-described objective and, as a result, found that the addition of arginine or a salt thereof to formulations comprising the above-described IL-31 antagonist (an anti-IL-31RA antibody (CIM331) in particular) increases stability of the formulations comprising the IL-31 antagonist regardless of the presence or absence of a lyophilization step. It was also found that the addition of sucrose or trehalose to the formulations increases stability of the formulations comprising the IL-31 antagonist when the formulations are in a lyophilized state. It was further found that the addition of a nonionic surfactant to the formulations increases stability of the formulations comprising the IL-31 antagonist when the formulations are in a solution state.

In a non-limiting embodiment, the present disclosure relates to the following.

[1] A lyophilized formulation comprising an IL-31 antagonist as an active ingredient, wherein the formulation comprises arginine and/or a salt thereof, sucrose and/or trehalose.
[2] The lyophilized formulation of [1], wherein the arginine and/or salt thereof is arginine-hydrochloride, arginine-aspartate, or arginine-glutamate.
[3] The lyophilized formulation of [1] or [2], wherein the arginine and/or salt thereof is arginine-hydrochloride (Arg-HCl).
[4] The lyophilized formulation of any one of [1] to [3], further comprising Tris buffer as a buffer agent.
[5] The lyophilized formulation of [4], wherein the Tris buffer is tris(hydroxymethyl)aminomethane and/or a salt thereof.
[6] The lyophilized formulation of [5], wherein the tris(hydroxymethyl)aminomethane and/or salt thereof is tris(hydroxymethyl)aminomethane-hydrochloride (Tris-HCl), tris(hydroxymethyl)aminomethane-aspartate, tris(hydroxymethyl)aminomethane-glutamate, or tris(hydroxymethyl)aminomethane-acetate.
[7] The lyophilized formulation of [5] or [6], wherein the tris(hydroxymethyl)aminomethane and/or salt thereof is tris(hydroxymethyl)aminomethane-hydrochloride (Tris-HCl).
[8] The lyophilized formulation of any one of [1] to [7], further comprising Poloxamer 188 or polysorbate as a nonionic surfactant.
[9] The lyophilized formulation of [8], wherein the polysorbate is Polysorbate 20 or Polysorbate 80.
[10] The lyophilized formulation of any one of [1] to [9], wherein pH is 6 to 8 when the formulation is reconstituted in water.

[11] The lyophilized formulation of any one of [1] to [10], wherein pH is 6.5 to 7.5 when the formulation is reconstituted in water.
[12] The lyophilized formulation of any one of [1] to [11], wherein pH is 7 when the formulation is reconstituted in water.
[13] A solution formulation comprising an IL-31 antagonist as an active ingredient, wherein the solution formulation comprises arginine and/or a salt thereof.
[14] The solution formulation of [13], wherein the arginine and/or salt thereof is arginine-hydrochloride (Arg-HCl), arginine-aspartate, or arginine-glutamate.
[15] The solution formulation of [13] or [14], wherein the arginine and/or salt thereof is arginine-hydrochloride (Arg-HCl).
[16] The solution formulation of any one of [13] to [15], further comprising Tris buffer as a buffer agent.
[17] The solution formulation of [16], wherein the Tris buffer is tris(hydroxymethyl)aminomethane and/or a salt thereof.
[18] The solution formulation of [17], wherein the tris(hydroxymethyl)aminomethane and/or salt thereof is tris(hydroxymethyl)aminomethane-hydrochloride (Tris-HCl), tris(hydroxymethyl)aminomethane-aspartate, tris(hydroxymethyl)aminomethane-glutamate, or tris(hydroxymethyl)aminomethane-acetate.
[19] The solution formulation of [17] or [18], wherein the tris(hydroxymethyl)aminomethane and/or salt thereof is tris(hydroxymethyl)aminomethane-hydrochloride (Tris-HCl).
[20] The solution formulation of any one of [13] to [19], further comprising a nonionic surfactant, wherein the nonionic surfactant is Poloxamer 188 or polysorbate.
[21] The solution formulation of [20], wherein the polysorbate is Polysorbate 20 or Polysorbate 80.
[22] The solution formulation of any one of [13] to [21], wherein pH is 6 to 8.
[23] The solution formulation of any one of [13] to [22], wherein pH is 6.5 to 7.5.
[24] The solution formulation of any one of [13] to [23], wherein pH is 7.
[25] A lyophilized formulation comprising an IL-31 antagonist as an active ingredient, which is a composition resulting from lyophilizing a solution comprising:
  1 to 200 mg/mL IL-31 antagonist;
  1 to 200 mmol/L Tris buffer;
  4.5 to 1500 mmol/L arginine or a salt thereof;
  7.5 to 2500 mmol/L sucrose or trehalose; and
  0.01 to 5 mg/mL Poloxamer 188 or Polysorbate 20,
wherein pH is 6 to 8 when the formulation is reconstituted in water:
[26] A lyophilized formulation comprising an IL-31 antagonist as an active ingredient, which is a composition resulting from lyophilizing a solution comprising:
  6 to 100 mg/mL IL-31 antagonist;
  6 to 20 mmol/L Tris buffer;
  45 to 150 mmol/L arginine or a salt thereof;
  75 to 250 mmol/L sucrose or trehalose; and
  0.15 to 0.50 mg/mL Poloxamer 188 or Polysorbate 20, wherein pH is 6 to 8 when the formulation is reconstituted in water:
[27] A lyophilized formulation comprising an IL-31 antagonist as an active ingredient, which comprises, per vial, cartridge, or syringe:
  1 to 800 mg IL-31 antagonist;
  0.1 to 40 mg tris(hydroxymethyl)aminomethane;
  0.8 to 400 mg arginine;
  3 to 1100 mg sucrose or trehalose; and
  0.01 to 7 mg Poloxamer 188 or Polysorbate 20, wherein pH is 6 to 8 when the formulation is reconstituted in water.
[28] A lyophilized formulation comprising an IL-31 antagonist as an active ingredient, which comprises, per vial, cartridge, or syringe:
  10 to 80 mg IL-31 antagonist;
  0.8 to 4 mg tris(hydroxymethyl)aminomethane;
  8 to 40 mg arginine;
  30 to 110 mg sucrose or trehalose; and
  0.1 to 0.7 mg Poloxamer 188 or Polysorbate 20, wherein pH is 6 to 8 when the formulation is reconstituted in water.
[29] The formulation of any one of [1] to [28], wherein the molar ratio of the arginine and/or salt thereof to the IL-31 antagonist is 220:1 to 1100:1, and/or the weight ratio of the arginine to the IL-31 antagonist is 0.3:1 to 1.3:1.
[30] The lyophilized formulation of any one of [1] to [12] and [25] to [28], wherein, between the sucrose or trehalose and the IL-31 antagonist, the molar ratio is 370:1 to 1840:1 and/or the weight ratio is 0.8:1 to 4.3:1.
[31] The lyophilized formulation of any one of [25] to [30], wherein the arginine and/or salt thereof is arginine-hydrochloride (Arg-HCl), arginine-aspartate, or arginine-glutamate.
[32] The lyophilized formulation of any one of [25] to [31], wherein the arginine and/or salt thereof is arginine-hydrochloride (Arg-HCl).
[33] The lyophilized formulation of [32], wherein the Tris buffer is tris(hydroxymethyl)aminomethane and/or a salt thereof.
[34] The lyophilized formulation of [33], wherein the tris(hydroxymethyl)aminomethane and/or a salt thereof is tris(hydroxymethyl)aminomethane-hydrochloride (Tris-HCl), tris(hydroxymethyl)aminomethane-aspartate, tris(hydroxymethyl)aminomethane-glutamate, or tris(hydroxymethyl)aminomethane-acetate.
[35] The lyophilized formulation of [33] or [34], wherein the tris(hydroxymethyl)aminomethane and/or a salt thereof is tris(hydroxymethyl)aminomethane-hydrochloride (Tris-HCl).
[36] The formulation of any one of [1] to [35], wherein the IL-31 antagonist is an antibody that inhibits IL-31 signaling.
[37] The formulation of [36], wherein the antibody that inhibits IL-31 signaling is an anti-IL-31 neutralizing antibody or an anti-IL-31RA neutralizing antibody.
[38] The formulation of [37], wherein the anti-IL-31RA neutralizing antibody is:
  (1) an anti-IL-31RA antibody comprising an H chain variable region which comprises CDR1 of SEQ ID NO: 1, CDR2 of SEQ ID NO: 2, and CDR3 of SEQ ID NO: 3, and an L chain variable region which comprises CDR1 of SEQ ID NO: 4, CDR2 of SEQ ID NO: 5, and CDR3 of SEQ ID NO: 6;
  (2) an anti-IL-31RA antibody comprising the H chain variable region of SEQ ID NO: 7 and the L chain variable region of SEQ ID NO: 8; or
  (3) an anti-IL-31RA antibody comprising the H chain of SEQ ID NO: 9 and the L chain of SEQ ID NO: 10.
[39] The formulation of [37] or [38], wherein the anti-IL-31RA neutralizing antibody is an IgG antibody, preferably an IgG2 antibody.
[40] The formulation of any one of [37] to [39], wherein the anti-IL-31RA neutralizing antibody is Nemolizumab.

[41] The lyophilized formulation of any one of [37] to [40], which is a composition resulting from lyophilizing a solution in which the concentration of the anti-IL-31RA neutralizing antibody is 68 mg/mL.
[42] The lyophilized formulation of any one of [37] to [40], which is a composition resulting from lyophilizing a solution in which the concentration of the anti-IL-31RA neutralizing antibody is 50 mg/mL.
[43] The lyophilized formulation of any one of [37] to [40], which is a composition resulting from lyophilizing a solution in which the concentration of the anti-IL-31RA neutralizing antibody is 15 mg/mL.
[44] The lyophilized formulation of any one of [37] to [40], which is a composition resulting from lyophilizing a solution in which the concentration of the anti-IL-31RA neutralizing antibody is 7.5 mg/mL.
[45] The lyophilized formulation of any one of [37] to [41], which is a composition resulting from lyophilizing a solution in which the concentration of the Tris-HCl is 13.6 mmol/L.
[46] The lyophilized formulation of any one of [37] to [40] and [42], which is a composition resulting from lyophilizing a solution in which the concentration of the Tris-HCl is 10 mmol/L.
[47] The lyophilized formulation of any one of [37] to [40] and [43] to [44], which is a composition resulting from lyophilizing a solution in which the concentration of the Tris-HCl is 6 mmol/L.
[48] The lyophilized formulation of any one of [37] to [41] and [45], which is a composition resulting from lyophilizing a solution in which the concentration of the Arg-HCl is 102 mmol/L.
[49] The lyophilized formulation of any one of [37] to [40], [42], and [46], which is a composition resulting from lyophilizing a solution in which the concentration of the Arg-HCl is 75 mmol/L.
[50] The lyophilized formulation of any one of [37] to [40], [43] to [44], and [47], which is a composition resulting from lyophilizing a solution in which the concentration of the Arg-HCl is 45 mmol/L.
[51] The lyophilized formulation of any one of [37] to [41], [45], and [48], which is a composition resulting from lyophilizing a solution in which the concentration of the sucrose or trehalose is 170 mmol/L.
[52] The lyophilized formulation of any one of [37] to [40], [42], [46], and [49], which is a composition resulting from lyophilizing a solution in which the concentration of the sucrose or trehalose is 125 mmol/L.
[53] The lyophilized formulation of any one of [37] to [40], [43] to [44], [47], and [50], which is a composition resulting from lyophilizing a solution in which the concentration of the sucrose or trehalose is 75 mmol/L.
[54] The lyophilized formulation of any one of [37] to [41], [45], [48], and [51], which is a composition resulting from lyophilizing a solution in which the concentration of Poloxamer 188 or Polysorbate 20 is 0.34 mg/mL.
[55] The lyophilized formulation of any one of [37] to [40], [42], [46], [49], and [52], which is a composition resulting from lyophilizing a solution in which the concentration of Poloxamer 188 or Polysorbate 20 is 0.25 mg/mL.
[56] The lyophilized formulation of any one of [37] to [40], [43] to [44], [47], [50], and [53], which is a composition resulting from lyophilizing a solution in which the concentration of Poloxamer 188 or Polysorbate 20 is 0.15 mg/mL.
[57] The lyophilized formulation of any one of [37] to [42], [45] to [46], [48] to [49], [51] to [52], and [54] to [55], which is a composition resulting from lyophilizing a solution in which, between the arginine and the anti-IL-31RA neutralizing antibody, the molar ratio is 220:1 and/or the weight ratio is 0.3:1.
[58] The lyophilized formulation of any one of [37] to [40], [43], [47], [50], [53], and [56], which is a composition resulting from lyophilizing a solution in which, between the arginine and the anti-IL-31RA neutralizing antibody, the molar ratio is 440:1 and/or the weight ratio is 0.5:1.
[59] The lyophilized formulation of any one of [37] to [40], [44], [47], [50], [53], and [56], which is a composition resulting from lyophilizing a solution in which, between the arginine and the anti-IL-31RA neutralizing antibody, the molar ratio is 880:1 and/or the weight ratio is 1.0:1 to 1.1:1.
[60] The lyophilized formulation of any one of [37] to [42], [45] to [46], [48] to [49], [51] to [52], [54] to [55], and [57], which is a composition resulting from lyophilizing a solution in which, between the sucrose and the anti-IL-31RA neutralizing antibody, the molar ratio is 370:1 and/or the weight ratio is 0.8:1 to 0.9:1.
[61] The lyophilized formulation of any one of [37] to [40], [43], [47], [50], [53], [56], and [58], which is a composition resulting from lyophilizing a solution in which, between the sucrose and the anti-IL-31RA neutralizing antibody, the molar ratio is 740:1 and/or the weight ratio is 1.7:1.
[62] The lyophilized formulation of any one of [37] to [40], [44], [47], [50], [53], [56], and [59], which is a composition resulting from lyophilizing a solution in which, between the sucrose and the anti-IL-31RA neutralizing antibody, the molar ratio is 1470:1 and/or the weight ratio is 3.4:1 to 3.5:1.
[63] The lyophilized formulation of any one of [25] to [62], wherein the pH when the formulation is reconstituted in water is 6.5 to 7.5.
[64] The lyophilized formulation of any one of [25] to [63], wherein the pH when the formulation is reconstituted in water is 7.
[65] The lyophilized formulation of any one of [25] to [40], which comprises, per container such as syringe:
75 mg anti-IL-31RA neutralizing antibody;
1.8 mg tris(hydroxymethyl)aminomethane;
19 mg arginine;
64 mg sucrose;
0.4 mg Poloxamer 188.
[66] The lyophilized formulation of any one of [25] to [40], which comprises, per container such as syringe:
75 mg anti-IL-31RA neutralizing antibody;
0.24 mg tris(hydroxymethyl)aminomethane;
23.6 mg L-arginine hydrochloride;
63.9 mg sucrose;
0.37 mg Poloxamer 188; and
tris(hydroxymethyl)aminomethane-hydrochloride as a pH adjusting agent.
[67] The lyophilized formulation of any one of [25] to [40], which comprises, per container such as syringe:
39 mg anti-IL-31RA neutralizing antibody;
0.9 mg tris(hydroxymethyl)aminomethane;
10 mg arginine;
33 mg sucrose; and
0.2 mg Poloxamer 188.
[68] The lyophilized formulation of any one of [25] to [40], which comprises, per container such as cartridge:
36 mg anti-IL-31RA neutralizing antibody;
0.9 mg tris(hydroxymethyl)aminomethane;
9 mg arginine;

31 mg sucrose; and
0.2 mg Poloxamer 188.

[69] The lyophilized formulation of any one of [25] to [40], which comprises, per container such as vial:
51 mg anti-IL-31RA neutralizing antibody;
2.5 mg tris(hydroxymethyl)aminomethane;
27 mg arginine;
88 mg sucrose; and
0.5 mg Poloxamer 188.

[70] The lyophilized formulation of any one of [25] to [40], which comprises, per container such as vial:
30 mg anti-IL-31RA neutralizing antibody;
3.0 mg tris(hydroxymethyl)aminomethane;
32 mg arginine;
104 mg sucrose; and
0.6 mg Poloxamer 188.

[71] The lyophilized formulation of any one of [25] to [40], which comprises, per container such as vial:
19 mg anti-IL-31RA neutralizing antibody;
1.9 mg tris(hydroxymethyl)aminomethane;
20 mg arginine;
66 mg sucrose; and
0.4 mg Poloxamer 188.

[72] The lyophilized formulation of any one of [25] to [40], which comprises, per container such as vial:
14 mg anti-IL-31RA neutralizing antibody;
1.3 mg tris(hydroxymethyl)aminomethane;
15 mg arginine;
47 mg sucrose; and
0.3 mg Poloxamer 188.

[73] The lyophilized formulation of any one of [25] to [40], which is a composition resulting from lyophilizing a solution comprising:
68 mg/mL anti-IL-31RA antibody which comprises the H chain of SEQ ID NO: 9 and the L chain of SEQ ID NO: 10;
13.6 mmol/L tris(hydroxymethyl)aminomethane-hydrochloride (Tris-HCl) buffer;
102 mmol/L arginine-hydrochloride (Arg-HCl);
170 mmol/L sucrose; and
0.34 mg/mL Poloxamer 188,
wherein pH is 7 when the formulation is reconstituted in water.

[74] The lyophilized formulation of any one of [25] to [40], which is a composition resulting from lyophilizing a solution comprising:
50 mg/mL anti-IL-31RA antibody which comprises the H chain of SEQ ID NO: 9 and the L chain of SEQ ID NO: 10;
10 mmol/L tris(hydroxymethyl)aminomethane-hydrochloride (Tris-HCl) buffer;
75 mmol/L arginine-hydrochloride (Arg-HCl);
125 mmol/L sucrose; and
0.25 mg/mL Poloxamer 188,
wherein pH is 7 when the formulation is reconstituted in water.

[75] The lyophilized formulation of any one of [25] to [40], which is a composition resulting from lyophilizing a solution comprising:
15 mg/mL anti-IL-31RA antibody which comprises the H chain of SEQ ID NO: 9 and the L chain of SEQ ID NO: 10;
6 mmol/L tris(hydroxymethyl)aminomethane-hydrochloride (Tris-HCl) buffer;
45 mmol/L arginine-hydrochloride (Arg-HCl);
75 mmol/L sucrose; and
0.15 mg/mL Poloxamer 188,
wherein pH is 7 when the formulation is reconstituted in water.

[76] The lyophilized formulation of any one of [25] to [40], which is a composition resulting from lyophilizing a solution comprising:
7.5 mg/mL anti-IL-31RA antibody which comprises the H chain of SEQ ID NO: 9 and the L chain of SEQ ID NO: 10;
6 mmol/L tris(hydroxymethyl)aminomethane-hydrochloride (Tris-HCl) buffer;
45 mmol/L arginine-hydrochloride (Arg-HCl);
75 mmol/L sucrose; and
0.15 mg/mL Poloxamer 188,
wherein pH is 7 when the formulation is reconstituted in water.

[77] A lyophilized formulation comprising an IL-31 antagonist as an active ingredient, the lyophilized formulation further comprising Tris buffer, arginine, sucrose or trehalose, and Poloxamer 188 or Polysorbate 20, wherein, when the formulation is reconstituted in water:
1 to 200 mg/mL IL-31 antagonist;
1 to 200 mmol/L Tris buffer;
4.5 to 1500 mmol/L arginine or a salt thereof;
7.5 to 2500 mmol/L sucrose or trehalose; and
0.01 to 5 mg/mL Poloxamer 188 or Polysorbate 20
are comprised, and pH is 6 to 8.

[78] A lyophilized formulation comprising an IL-31 antagonist as an active ingredient, the lyophilized formulation further comprising Tris buffer, arginine, sucrose or trehalose, and Poloxamer 188 or Polysorbate 20, wherein, when the formulation is reconstituted in water:
20 to 100 mg/mL IL-31 antagonist;
10 to 20 mmol/L Tris buffer;
75 to 150 mmol/L arginine or a salt thereof;
125 to 250 mmol/L sucrose or trehalose; and
0.25 to 0.50 mg/mL Poloxamer 188 or Polysorbate 20
are comprised, and pH is 6 to 8.

[79] The lyophilized formulation of [77] or [78], wherein the molar ratio of the arginine and/or salt thereof to the IL-31 antagonist is 220:1 to 1100:1, and/or the weight ratio of the arginine to the IL-31 antagonist is 0.3:1 to 1.3:1.

[80] The lyophilized formulation of any one of [77] to [79], wherein, between the sucrose or trehalose and the IL-31 antagonist, the molar ratio is 370:1 to 1840:1 and/or the weight ratio is 0.8:1 to 4.3:1.

[81] The lyophilized formulation of any one of [77] to [80], wherein the arginine and/or salt thereof is arginine-hydrochloride (Arg-HCl), arginine-aspartate, or arginine-glutamate.

[82] The lyophilized formulation of any one of [77] to [81], wherein the arginine and/or salt thereof is arginine-hydrochloride (Arg-HCl).

[83] The lyophilized formulation of any one of [77] to [82], wherein the Tris buffer is tris(hydroxymethyl)aminomethane and/or a salt thereof.

[84] The lyophilized formulation of [83], wherein the tris(hydroxymethyl)aminomethane and/or a salt thereof is tris(hydroxymethyl)aminomethane-hydrochloride (Tris-HCl), tris(hydroxymethyl)aminomethane-aspartate, tris(hydroxymethyl)aminomethane-glutamate, or tris(hydroxymethyl)aminomethane-acetate.

[85] The lyophilized formulation of [83] or [84], wherein the tris(hydroxymethyl)aminomethane and/or a salt thereof is tris(hydroxymethyl)aminomethane-hydrochloride (Tris-HCl).

[86] The lyophilized formulation of any one of [77] to [85], wherein the IL-31 antagonist is an antibody that inhibits IL-31 signaling.

[87] The lyophilized formulation of [86], wherein the antibody that inhibits IL-31 signaling is an anti-IL-31 neutralizing antibody or an anti-IL-31RA neutralizing antibody.

[88] The lyophilized formulation of [87], wherein the anti-IL-31RA neutralizing antibody is:
(1) an anti-IL-31RA antibody comprising an H chain variable region which comprises CDR1 of SEQ ID NO: 1, CDR2 of SEQ ID NO: 2, and CDR3 of SEQ ID NO: 3, and an L chain variable region which comprises CDR1 of SEQ ID NO: 4, CDR2 of SEQ ID NO: 5, and CDR3 of SEQ ID NO: 6;
(2) an anti-IL-31RA antibody comprising the H chain variable region of SEQ ID NO: 7 and the L chain variable region of SEQ ID NO: 8; or
(3) an anti-IL-31RA antibody comprising the H chain of SEQ ID NO: 9 and the L chain of SEQ ID NO: 10.

[89] The lyophilized formulation of [87] or [88], wherein the anti-IL-31RA neutralizing antibody is an IgG antibody, preferably an IgG2 antibody.

[90] The lyophilized formulation of any one of [87] to [89], wherein the anti-IL-31RA neutralizing antibody is Nemolizumab.

[91] The lyophilized formulation of any one of [87] to [90], wherein the concentration of the anti-IL-31RA neutralizing antibody when the formulation is reconstituted in water is 100 mg/mL.

[92] The lyophilized formulation of any one of [87] to [90], wherein the concentration of the anti-IL-31RA neutralizing antibody when the formulation is reconstituted in water is 61.5 mg/mL.

[93] The lyophilized formulation of any one of [87] to [90], wherein the concentration of the anti-IL-31RA neutralizing antibody when the formulation is reconstituted in water is 50 mg/mL.

[94] The lyophilized formulation of any one of [87] to [90], wherein the concentration of the anti-IL-31RA neutralizing antibody when the formulation is reconstituted in water is 25 mg/mL.

[95] The lyophilized formulation of any one of [87] to [91], wherein the concentration of the Tris-HCl when the formulation is reconstituted in water is 20 mmol/L.

[96] The lyophilized formulation of any one of [87] to [90] and [92] wherein the concentration of the Tris-HCl when the formulation is reconstituted in water is 12.3 mmol/L.

[97] The lyophilized formulation of any one of [87] to [90] and [93] to [94], wherein the concentration of the Tris-HCl when the formulation is reconstituted in water is 20 mmol/L.

[98] The lyophilized formulation of any one of [87] to [91] and [95], wherein the concentration of the Arg-HCl when the formulation is reconstituted in water is 150 mmol/L.

[99] The lyophilized formulation of any one of [87] to [90], [92], and [96], wherein the concentration of the Arg-HCl when the formulation is reconstituted in water is 92 mmol/L.

[100] The lyophilized formulation of any one of [87] to [90], [93] to [94], and [97], wherein the concentration of the Arg-HCl when the formulation is reconstituted in water is 150 mmol/L.

[101] The lyophilized formulation of any one of [87] to [91], [95], and [98], wherein the concentration of the sucrose or trehalose when the formulation is reconstituted in water is 250 mmol/L.

[102] The lyophilized formulation of any one of [87] to [90], [92], [96], and [99], wherein the concentration of the sucrose or trehalose when the formulation is reconstituted in water is 154 mmol/L.

[103] The lyophilized formulation of any one of [87] to [90], [93] to [94], [97], and [100], wherein the concentration of the sucrose or trehalose when the formulation is reconstituted in water is 250 mmol/L.

[104] The lyophilized formulation of any one of [87] to [91], [95], [98], and [101], wherein the concentration of Poloxamer 188 or Polysorbate 20 when the formulation is reconstituted in water is 0.50 mg/mL.

[105] The lyophilized formulation of any one of [87] to [90], [92], [96], [99], and [102], wherein the concentration of Poloxamer 188 or Polysorbate 20 when the formulation is reconstituted in water is 0.31 mg/mL.

[106] The lyophilized formulation of any one of [87] to [90], [93] to [94], [97], [100], and [103], wherein the concentration of Poloxamer 188 or Polysorbate 20 when the formulation is reconstituted in water is 0.50 mg/mL.

[107] The lyophilized formulation of any one of [87] to [91], [95], [98], [101], and [104] to [105], wherein, between the arginine and the anti-IL-31RA neutralizing antibody, the molar ratio is 220:1 and/or the weight ratio is 0.3:1.

[108] The lyophilized formulation of any one of [87] to [90], [93], [97], [100], [103], and [106], wherein, between the arginine and the anti-IL-31RA neutralizing antibody, the molar ratio is 440:1 and/or the weight ratio is 0.5:1.

[109] The lyophilized formulation of any one of [87] to [90], [94], [97], [100], [103], and [106], wherein, between the arginine and the anti-IL-31RA neutralizing antibody, the molar ratio is 880:1 and/or the weight ratio is 1.0:1 to 1.1:1.

[110] The lyophilized formulation of any one of [87] to [91], [95], [98], [101], [104] to [105], and [107], wherein, between the sucrose and the anti-IL-31RA neutralizing antibody, the molar ratio is 370:1 and/or the weight ratio is 0.8:1 to 0.9:1.

[111] The lyophilized formulation of any one of [87] to [90], [93], [97], [100], [103], [106], and [108], wherein, between the sucrose and the anti-IL-31RA neutralizing antibody, the molar ratio is 740:1 and/or the weight ratio is 1.7:1.

[112] The lyophilized formulation of any one of [87] to [90], [94], [97], [100], [103], and [109], wherein, between the sucrose and the anti-IL-31RA neutralizing antibody, the molar ratio is 1470:1 and/or the weight ratio is 3.4:1 to 3.5:1.

[113] The lyophilized formulation of any one of [77] to [112], wherein the pH when the formulation is reconstituted in water is 6.5 to 7.5.

[114] The lyophilized formulation of any one of [77] to [113], wherein the pH when the formulation is reconstituted in water is 6.7 to 7.3.

[115] The lyophilized formulation of any one of [77] to [114], wherein the pH when the formulation is reconstituted in water is 7.

[116] The lyophilized formulation of any one of [87] to [91], [95], [98], [101], [104], [107], and [110], wherein the lyophilized formulation is a pharmaceutical composition comprising as an active ingredient an anti-IL-31RA antibody which comprises the H chain of SEQ ID NO: 9 and the L chain of SEQ ID NO: 10, and is prepared by freeze-drying a solution comprising a buffer, a stabilizer, an excipient, and a nonionic surfactant, and wherein the following concentrations are made when the lyophilized formulation is reconstituted in water:

the anti-IL-31RA neutralizing antibody at 100 mg/mL;
tris(hydroxymethyl)aminomethane-hydrochloride (Tris-HCl) buffer at 20 mmol/L;
arginine-hydrochloride (Arg-HCl) at 150 mmol/L;
sucrose at 250 mmol/L; and
Poloxamer 188 at 0.50 mg/mL.

[117] The lyophilized formulation of any one of [87] to [90], [92], [96], [99], [102], [105], [107], and [110], wherein the lyophilized formulation is a pharmaceutical composition comprising as an active ingredient an anti-IL-31RA antibody which comprises the H chain of SEQ ID NO: 9 and the L chain of SEQ ID NO: 10, and is prepared by freeze-drying a solution comprising a buffer, a stabilizer, an excipient, and a nonionic surfactant, and the following concentrations are made when the lyophilized formulation is reconstituted in water:
the anti-IL-31RA neutralizing antibody at 61.5 mg/mL;
tris(hydroxymethyl)aminomethane-hydrochloride (Tris-HCl) buffer at 12.3 mmol/L;
arginine-hydrochloride (Arg-HCl) at 92 mmol/L;
sucrose at 154 mmol/L; and
Poloxamer 188 at 0.31 mg/mL.

[118] The lyophilized formulation of any one of [87] to [90], [93], [97], [100], [103], [106], [108], and [111], wherein the lyophilized formulation is a pharmaceutical composition comprising as an active ingredient an anti-IL-31RA antibody which comprises the H chain of SEQ ID NO: 9 and the L chain of SEQ ID NO: 10, and is prepared by freeze-drying a solution comprising a buffer, a stabilizer, an excipient, and a nonionic surfactant, and wherein the following concentrations are made when the lyophilized formulation is reconstituted in water:
the anti-IL-31RA neutralizing antibody at 50 mg/mL;
tris(hydroxymethyl)aminomethane-hydrochloride (Tris-HCl) buffer at 20 mmol/L;
arginine-hydrochloride (Arg-HCl) at 150 mmol/L;
sucrose at 250 mmol/L; and
Poloxamer 188 at 0.50 mg/mL

[119] The lyophilized formulation of any one of [87] to [90], [94], [97], [100], [103], [109], and [112], wherein the lyophilized formulation is a pharmaceutical composition comprising as an active ingredient an anti-IL-31RA antibody which comprises the H chain of SEQ ID NO: 9 and the L chain of SEQ ID NO: 10, and is prepared by freeze-drying a solution comprising a buffer, a stabilizer, an excipient, and a nonionic surfactant, and wherein the following concentrations are made when the lyophilized formulation is reconstituted in water:
the anti-IL-31RA neutralizing antibody at 25 mg/mL;
tris(hydroxymethyl)aminomethane-hydrochloride (Tris-HCl) buffer at 20 mmol/L;
arginine-hydrochloride (Arg-HCl) at 150 mmol/L;
sucrose at 250 mmol/L; and
Poloxamer 188 at 0.50 mg/mL.

[120] A lyophilized formulation comprising an IL-31 antagonist as an active ingredient, which is a composition resulting from lyophilizing a solution comprising:
1 to 200 mg/mL IL-31 antagonist;
1 to 200 mmol/L Tris buffer;
4.5 to 1500 mmol/L arginine or a salt thereof;
7.5 to 2500 mmol/L sucrose or trehalose; and
0.01 to 5 mg/mL Poloxamer 188 or Polysorbate 20,
wherein, when the formulation is reconstituted in water:
1 to 200 mg/mL IL-31 antagonist;
1 to 200 mmol/L Tris buffer;
4.5 to 1500 mmol/L arginine or a salt thereof;
7.5 to 2500 mmol/L sucrose or trehalose; and
0.01 to 5 mg/mL Poloxamer 188 or Polysorbate 20
are comprised, and pH is 6 to 8.

[121] A lyophilized formulation comprising an IL-31 antagonist as an active ingredient, which is a composition resulting from lyophilizing a solution comprising:
6 to 100 mg/mL IL-31 antagonist;
6 to 20 mmol/L Tris buffer;
45 to 150 mmol/L arginine or a salt thereof;
75 to 250 mmol/L sucrose or trehalose; and
0.15 to 0.50 mg/mL Poloxamer 188 or Polysorbate 20,
wherein, when the formulation is reconstituted in water:
20 to 100 mg/mL IL-31 antagonist;
10 to 20 mmol/L Tris buffer;
75 to 150 mmol/L arginine or a salt thereof;
125 to 250 mmol/L sucrose or trehalose; and
0.25 to 0.50 mg/mL Poloxamer 188 or Polysorbate 20
are comprised, and pH is 6 to 8.

[122] The lyophilized formulation of [120] or [121], wherein the molar ratio of the arginine and/or salt thereof to the IL-31 antagonist is 220:1 to 1100:1.

[123] The lyophilized formulation of any one of [120] to [122], wherein the molar ratio of the sucrose or trehalose to the IL-31 antagonist is 370:1 to 1840:1.

[124] The lyophilized formulation of any one of [120] to [123], wherein the arginine and/or salt thereof is arginine-hydrochloride (Arg-HCl), arginine-aspartate, or arginine-glutamate.

[125] The lyophilized formulation of any one of [120] to [124], wherein the arginine and/or salt thereof is arginine-hydrochloride (Arg-HCl).

[126] The lyophilized formulation of any one of [120] to [125], wherein the Tris buffer is tris(hydroxymethyl)aminomethane and/or a salt thereof.

[127] The lyophilized formulation of any one of [120] to [126], wherein the tris(hydroxymethyl)aminomethane and/or a salt thereof is tris(hydroxymethyl)aminomethane-hydrochloride (Tris-HCl), tris(hydroxymethyl)aminomethane-aspartate, tris(hydroxymethyl)aminomethane-glutamate, or tris(hydroxymethyl)aminomethane-acetate.

[128] The lyophilized formulation of any one of [120] or [127], wherein the tris(hydroxymethyl)aminomethane and/or a salt thereof is tris(hydroxymethyl)aminomethane-hydrochloride (Tris-HCl).

[129] The lyophilized formulation of any one of [120] to [128], wherein the IL-31 antagonist is an antibody that inhibits IL-31 signaling.

[130] The lyophilized formulation of [129], wherein the antibody that inhibits IL-31 signaling is an anti-IL-31 neutralizing antibody or an anti-IL-31RA neutralizing antibody.

[131] The lyophilized formulation of [130], wherein the anti-IL-31RA neutralizing antibody is:
(1) an anti-IL-31RA antibody comprising an H chain variable region which comprises CDR1 of SEQ ID NO: 1, CDR2 of SEQ ID NO: 2, and CDR3 of SEQ ID NO: 3, and an L chain variable region which comprises CDR1 of SEQ ID NO: 4, CDR2 of SEQ ID NO: 5, and CDR3 of SEQ ID NO: 6;
(2) an anti-IL-31RA antibody comprising the H chain variable region of SEQ ID NO: 7 and the L chain variable region of SEQ ID NO: 8; or
(3) an anti-IL-31RA antibody comprising the H chain of SEQ ID NO: 9 and the L chain of SEQ ID NO: 10.

[132] The lyophilized formulation of [130] or [131], wherein the anti-IL-31RA neutralizing antibody is an IgG antibody, preferably an IgG2 antibody.

[133] The lyophilized formulation of any one of [130] to [132], wherein the anti-IL-31RA neutralizing antibody is Nemolizumab.

[134] The formulation of any one of [1] to [133], for preventing and/or treating an IL-31-associated disorder or a symptom accompanying with the disorder.

[135] The formulation of [134], wherein the IL-31-associated disorder is an inflammatory disease related to IL-31 signaling.

[136] The formulation of [135], wherein the inflammatory disease is selected from the group consisting of atopic dermatitis, dialysis-induced pruritus, and prurigo nodularis.

[137] The formulation of any one of [1] to [136], wherein the IL-31 antagonist is subcutaneously administered.

[138] A method for stabilizing an antibody in an antibody-containing formulation, comprising preparing an antibody-containing solution which comprises arginine and/or a salt thereof, and/or sucrose and/or trehalose, wherein, in the solution, the molar ratio of the arginine and/or salt thereof to the antibody is 220:1 to 1100:1 and the molar ratio of the sucrose or trehalose to the antibody is 370:1 to 1840:1.

[139] The method of [138], wherein the antibody-containing solution further comprises 6 to 20 mmol/L tris(hydroxymethyl)aminomethane-hydrochloride (Tris-HCl) buffer and 0.15 to 0.50 mg/mL Poloxamer 188.

[140] The method of [138] or [139], further comprising preparing an antibody-containing lyophilized formulation by freeze-drying the antibody-containing solution.

[141] Use of arginine and/or a salt thereof, and/or sucrose and/or trehalose for stabilizing an antibody in an antibody-containing formulation, comprising preparing an antibody-containing solution which comprises arginine and/or a salt thereof, and/or sucrose and/or trehalose, wherein, in the solution, the molar ratio of the arginine and/or salt thereof to the antibody is 220:1 to 1100:1 and the molar ratio of the sucrose or trehalose to the antibody is 370:1 to 1840:1.

[142] The use of [141], wherein the antibody-containing solution further comprises 6 to 20 mmol/L tris(hydroxymethyl)aminomethane-hydrochloride (Tris-HCl) buffer and 0.15 to 0.50 mg/mL Poloxamer 188.

[143] The use of [141] or [142], further comprising preparing an antibody-containing lyophilized formulation by freeze-drying the antibody-containing solution.

[144] A method for suppressing antibody aggregation (aggregate formation) in an antibody-containing formulation, comprising preparing an antibody-containing solution which comprises arginine and/or a salt thereof, and/or sucrose and/or trehalose, wherein in the solution the molar ratio of the arginine and/or salt thereof to the antibody is 220:1 to 1100:1 and the molar ratio of the sucrose or trehalose to the antibody is 370:1 to 1840:1.

[145] The method of [144], wherein the antibody-containing solution further comprises 6 to 20 mmol/L tris(hydroxymethyl)aminomethane-hydrochloride (Tris-HCl) buffer and 0.15 to 0.50 mg/mL Poloxamer 188.

[146] The method of [144] or [145], further comprising preparing an antibody-containing lyophilized formulation by freeze-drying the antibody-containing solution.

[147] Use of arginine and/or a salt thereof, and/or sucrose and/or trehalose for suppressing antibody aggregation (aggregate formation) in an antibody-containing formulation, comprising preparing an antibody-containing solution which comprises arginine and/or a salt thereof, and/or sucrose and/or trehalose, wherein, in the solution, the molar ratio of the arginine and/or salt thereof to the antibody is 220:1 to 1100:1 and the molar ratio of the sucrose or trehalose to the antibody is 370:1 to 1840:1.

[148] The use of [147], wherein the antibody-containing solution further comprises 6 to 20 mmol/L tris(hydroxymethyl)aminomethane-hydrochloride (Tris-HCl) buffer and 0.15 to 0.50 mg/mL Poloxamer 188.

[149] The use of [147] or [148], further comprising preparing an antibody-containing lyophilized formulation by freeze-drying the antibody-containing solution.

[150] A method for reducing components with charge heterogeneity in an antibody-containing formulation, comprising preparing an antibody-containing solution which comprises arginine and/or a salt thereof, and/or sucrose and/or trehalose, wherein, in the solution, the molar ratio of the arginine and/or salt thereof to the antibody is 220:1 to 1100:1 and the molar ratio of the sucrose or trehalose to the antibody is 370:1 to 1840:1.

[151] The method of [150], wherein the antibody-containing solution further comprises 6 to 20 mmol/L tris(hydroxymethyl)aminomethane-hydrochloride (Tris-HCl) buffer and 0.15 to 0.50 mg/mL Poloxamer 188.

[152] The method of [150] or [151], further comprising preparing an antibody-containing lyophilized formulation by freeze-drying the antibody-containing solution.

[153] Use of arginine and/or a salt thereof, and/or sucrose and/or trehalose for reducing components with charge heterogeneity in an antibody-containing formulation, comprising preparing an antibody-containing solution which comprises arginine and/or a salt thereof, and/or sucrose and/or trehalose, wherein, in the solution, the molar ratio of the arginine and/or salt thereof to the antibody is 220:1 to 1100:1 and the molar ratio of the sucrose or trehalose to the antibody is 370:1 to 1840:1.

[154] The use of [153], wherein the antibody-containing solution further comprises 6 to 20 mmol/L tris(hydroxymethyl)aminomethane-hydrochloride (Tris-HCl) buffer and 0.15 to 0.50 mg/mL Poloxamer 188.

[155] The use of [153] or [154], further comprising preparing an antibody-containing lyophilized formulation by freeze-drying the antibody-containing solution.

[156] A method for preventing and/or treating an IL-31-associated disorder, comprising administering an IL-31 antagonist to a subject affected with or at a risk of being affected with the IL-31-associated disorder, the method comprising:
preparing a lyophilized formulation by freeze-drying a solution comprising 6 to 100 mg/mL IL-31 antagonist, 45 to 150 mmol/L arginine-hydrochloride (Arg-HCl), and 75 to 250 mmol/L sucrose or trehalose;
preparing a reconstituted solution by reconstituting the lyophilized formulation in water; and administering the reconstituted solution to the subject.

[157] Use of an IL-31 antagonist in the manufacture of a medicament for preventing and/or treating an IL-31-associated disorder, characterized in that a lyophilized formulation is prepared by freeze-drying a solution comprising 6 to 100 mg/mL IL-31 antagonist, 45 to 150 mmol/L arginine-hydrochloride (Arg-HCl), and 75 to 250 mmol/L sucrose or trehalose.

[158] An IL-31 antagonist for use in preventing and/or treating an IL-31-associated disorder, characterized in that a lyophilized formulation resulting from lyophilizing a solution comprising 6 to 100 mg/mL IL-31 antagonist, 45 to 150 mmol/L arginine-hydrochloride (Arg-HCl), and 75 to 250 mmol/L sucrose or trehalose is reconstituted in water prior to use.

[159] The method of [156], the use of [157], or the IL-31 antagonist of [158], wherein the solution before lyophilization further comprises 6 to 20 mmol/L tris(hydroxymethyl)aminomethane-hydrochloride (Tris-HCl) buffer and 0.15 to 0.50 mg/mL Poloxamer 188.

[160] A formulation for injection or a kit comprising (i) a container, (ii) the lyophilized formulation of any one of [1] to [12] and [25] to [137], and (iii) water for injection for reconstituting the lyophilized formulation.

[161] A formulation for injection comprising (i) a container, (ii) a lyophilized formulation in the container, the lyophilized formulation resulting from lyophilizing a solution comprising 6 to 100 mg/mL anti-IL-31RA neutralizing antibody, 45 to 150 mmol/L arginine-hydrochloride (Arg-HCl), and 75 to 250 mmol/L sucrose or trehalose, and (iii) optionally, water for injection for reconstituting the lyophilized formulation.

[162] The formulation for injection of [161], wherein the solution before lyophilization further comprises 6 to 20 mmol/L tris(hydroxymethyl)aminomethane-hydrochloride (Tris-HCl) buffer and 0.15 to 0.50 mg/mL Poloxamer 188.

[163] A formulation for injection comprising (i) a container, (ii) a lyophilized formulation in the container, the lyophilized formulation resulting from lyophilizing a solution comprising an effective amount of anti-IL-31RA neutralizing antibody, and 220 to 1100 mole of arginine-hydrochloride (Arg-HCl) and 370 to 1840 mole of sucrose or trehalose per 1 mole of the antibody, and (iii) optionally, water for injection for reconstituting the lyophilized formulation.

[164] The formulation for injection or kit of any one of [160] to [163], wherein the lyophilized formulation and the water for injection are enclosed in separate compartments in the container.

[165] The formulation for injection or kit of any one of [160] to [164], wherein the lyophilized formulation is reconstituted using the water for injection within the container when used.

DESCRIPTION OF EMBODIMENTS

Preferred non-limiting embodiments of the present disclosure will be hereinafter described.

All the embodiments set forth in the Examples below are described with the intention that they are naturally construed as being equivalently described in the "Description of Embodiments" of the present specification, without being restricted by any patent practice, conventions, or law that may interpret the contents of the Examples in a limiting manner, in a country where it is intended that the protection of the present patent application be sought.

For descriptions for numerical values in the present disclosure, a numerical value at the smallest digit (for example, ones place) may include values in which one place smaller than the smallest digit (for example, when the smallest digit is ones place, first decimal place) is rounded off. For example, it is intended that the numerical value "5" comprises numerical values comprised in the rages of 4.5 to 5.4.

In a non-limiting embodiment, the present disclosure relates to a lyophilized formulation comprising an IL-31 antagonist as an active ingredient, the lyophilized formulation comprising arginine and/or salts thereof, and sucrose and/or trehalose. In another non-limiting embodiment, the present disclosure relates to a solution formulation comprising an IL-31 antagonist as an active ingredient, the solution formulation comprising arginine and/or salts thereof. Arginine is preferably L-arginine. In one embodiment, arginine and/or a salt thereof is arginine-hydrochloride, L-arginine-hydrochloride, arginine-aspartate, L-arginine-aspartate, arginine-glutamate, or L-arginine-glutamate. Those skilled in the art will understand that, when the weight (e.g., mg) of arginine is referred to, the weight may be the weight of free arginine, or the weight of arginine contained in a salt comprising arginine. Furthermore, in the present disclosure, the weight or concentration of arginine may be a sum of the weight or concentration of free arginine and the weight or concentration of arginine contained in a salt comprising arginine. In one embodiment, the formulation of the present disclosure further comprises Tris buffer as a buffer. In one embodiment, Tris buffer is tris(hydroxymethyl)aminomethane and/or a salt thereof, for example tris(hydroxymethyl)aminomethane-hydrochloride (Tris-HCl), tris(hydroxymethyl)aminomethane-aspartate, tris(hydroxymethyl)aminomethane-glutamate, or tris(hydroxymethyl)aminomethane-acetate. In one embodiment, the formulation of the present disclosure further comprises Poloxamer 188 or polysorbate as a nonionic surfactant. Poloxamer 188 may be called "polyoxyethylene (160) polyoxypropylene (30) glycol" in Standards of Pharmacopoeia of Japan. In one embodiment, polysorbate is Polysorbate 20 or Polysorbate 80. In one embodiment, pH of a reconstituted solution after reconstituting the lyophilized formulation of the present disclosure in water is 6 to 8, for example 6.5 to 7.5, for example 6.7 to 7.3, and for example 7. In one embodiment, pH of the solution formulation of the present disclosure is 6 to 8, for example 6.5 to 7.5, and for example 7. Meanwhile, tris(hydroxymethyl)aminomethane may be called "Trometamol" in Standards of Pharmacopoeia of Japan. Those skilled in the art will understand that, when the weight (e.g., mg) of tris(hydroxymethyl)aminomethane is mentioned, the weight may be the weight of free tris(hydroxymethyl)aminomethane or the weight of tris(hydroxymethyl)aminomethane contained in a salt comprising tris(hydroxymethyl)aminomethane. Furthermore, in the present disclosure, the weight or concentration of tris(hydroxymethyl)aminomethane may be a sum of the weight or concentration of free tris(hydroxymethyl)aminomethane and the weight or concentration of tris(hydroxymethyl)aminomethane included in salts comprising tris(hydroxymethyl)aminomethane.

Amount and concentration of IL-31 antagonist comprised in the formulations of the present disclosure are not particularly limited, and can be adjusted appropriately depending on a subject to be administrated, for example, whether the formulations are for adults or for children, or whether the formulations are for prevention or for treatment, or depending on type, severity, and such of disorders or symptoms to be prevented or treated. Therefore, molar ratio and weight ratio of IL-31 antagonist to another component comprised in the formulation of the present disclosure can be various values. In a non-limiting embodiment, the molar ratio of arginine and/or a salt thereof to IL-31 antagonist is 3:1 to 220500:1, for example 22:1 to 6600:1, 33:1 to 5500:1, 44:1 to 4400:1, 55:1 to 3300:1, 110:1 to 2200:1, 220:1 to 1100:1, 220:1 to 880:1, 220:1 to 440:1, or 440:1 to 880:1. In a non-limiting embodiment, the weight ratio of arginine to IL-31 antagonist is 0.004:1 to 261:1, for example 0.03:1 to 9.6:1, 0.1:1 to 4.8:1, 0.2:1 to 3.2:1, 0.3:1 to 1.6:1, 0.3:1 to 1.3:1, 0.3:1 to 1.1:1, 0.5:1 to 1.1:1, or 0.3:1 to 0.5:1. In a non-limiting embodiment, the molar ratio of sucrose or trehalose to IL-31 antagonist is 6:1 to 367500:1, for example 75:1 to 7360:1, 100:1 to 5520:1, 150:1 to 3680:1, 300:1 to 1840:1, 370:1 to 1840:1, 370:1 to 1470:1, 740:1 to 1470:1, or 370:1 to 740:1. In a non-limiting embodiment, the weight ratio of sucrose or trehalose to IL-31 antagonist is 0.013:1 to 856:1, for example 0.18:1 to 16.8:1, 0.23:1 to 12.6:1, 0.35:1 to 8.4:1, 0.7:1 to 4.2:1, 0.8:1 to 4.3:1, 0.8:1 to 3.5:1, 1.7:1 to 3.5:1, or 0.8:1 to 1.7:1. Meanwhile, sucrose may be called "Seisei Hakutou (purified sucrose)" in Standards of Pharmacopoeia of Japan.

In a non-limiting embodiment, the concentration of an IL-31 antagonist comprised in the formulation of the present disclosure in a solution state (i.e., concentration in a solution formulation, concentration in a solution before lyophilization of a lyophilized solution, or concentration in a solution after redissolution of a lyophilized formulation) is 1 mg/mL to 200 mg/mL, for example 2 mg/mL to 200 mg/mL, 3 mg/mL to 200 mg/mL, 3 mg/mL to 150 mg/mL, 6 mg/mL to 100 mg/mL, 10 mg/mL to 100 mg/mL, 15 mg/mL to 100 mg/mL, 30 mg/mL to 100 mg/mL, 50 mg/mL to 100 mg/mL, 6 mg/mL to 70 mg/mL, 10 mg/mL to 70 mg/mL, 15 mg/mL to 70 mg/mL, 30 mg/mL to 70 mg/mL, 50 mg/mL to 70 mg/mL, 6 mg/mL to 50 mg/mL, 10 mg/mL to 50 mg/mL, 30 mg/mL to 50 mg/mL, or 6 mg/mL to 30 mg/mL.

In one embodiment, the concentration of arginine and/or a salt thereof comprised in the formulation of the present disclosure in a solution state is 4.5 mmol/L to 1500 mmol/L, for example 9 mmol/L to 750 mmol/L, 15 mmol/L to 450 mmol/L, 22.5 mmol/L to 300 mmol/L, 45 mmol/L to 150 mmol/L, 75 mmol/L to 150 mmol/L, or 45 mmol/L to 75 mmol/L.

In one embodiment, the concentration of sucrose and/or trehalose comprised in the formulation of the present disclosure in a solution state is 7.5 mmol/L to 2500 mmol/L, for example 15 mmol/L to 1250 mmol/L, 25 mmol/L to 750 mmol/L, 37.5 mmol/L to 500 mmol/L, 75 mmol/L to 250 mmol/L, 125 mmol/L to 250 mmol/L, 75 mmol/L to 170 mmol/L, 125 mmol/L to 170 mmol/L, or 75 mmol/L to 125 mmol/L.

In one embodiment, the concentration of Tris buffer comprised in the formulation of the present disclosure in a solution state is 1 mmol/L to 200 mmol/L, for example 1 mmol/L to 100 mmol/L, 2 mmol/L to 60 mmol/L, 3 mmol/L to 40 mmol/L, 6 mmol/L to 20 mmol/L, 3 mmol/L to 15 mmol/L, 10 mmol/L to 20 mmol/L, 10 mmol/L to 15 mmol/L, 6 mmol/L to 15 mmol/L, or 6 mmol/L to 10 mmol/L.

In one embodiment, the concentration of Poloxamer188 or polysorbate comprised in the formulation of the present disclosure in a solution state is 0.015 mg/mL to 5 mg/mL, for example 0.03 mg/mL to 2.5 mg/mL, 0.05 mg/mL to 1.5 mg/mL, 0.075 mg/mL to 1 mg/mL, 0.15 mg/mL to 0.5 mg/mL, 0.15 mg/mL to 0.4 mg/mL, 0.25 mg/mL to 0.5 mg/mL, or 0.15 mg/mL to 0.25 mg/mL.

In one embodiment, the lyophilized formulation of the present disclosure is a composition resulting from lyophilizing a solution comprising:
1 mg/mL to 200 mg/mL IL-31 antagonist;
1 mmol/L to 200 mmol/L Tris buffer;
4.5 mmol/L to 1500 mmol/L arginine or a salt thereof;
7.5 mmol/L to 2500 mmol/L sucrose or trehalose; and
0.01 mg/mL to 5 mg/mL Poloxamer 188 or Polysorbate 20,
wherein, when the formulation is reconstituted in water, pH is 6 to 8, for example 6.5 to 7.5, and for example 7.

In a particular embodiment, the lyophilized formulation of the present disclosure is a composition resulting from lyophilizing a solution comprising:
6 mg/mL to 100 mg/mL IL-31 antagonist;
6 mmol/L to 20 mmol/L Tris buffer;
45 mmol/L to 150 mmol/L arginine or a salt thereof;
75 mmol/L to 250 mmol/L sucrose or trehalose; and
0.15 mg/mL to 0.50 mg/mL Poloxamer 188 or Polysorbate 20,
wherein, when the formulation is reconstituted in water, pH is 6 to 8, for example 6.5 to 7.5, and for example 7.

In a particular embodiment, the lyophilized formulation of the present disclosure is a composition resulting from lyophilizing a solution comprising, per vial, cartridge, or syringe:
1 mg to 800 mg of IL-31 antagonist;
0.1 mg to 40 mg of tris(hydroxymethyl)aminomethane;
0.8 mg to 400 mg of arginine;
3 mg to 1100 mg of sucrose or trehalose; and
0.01 mg to 7 mg of Poloxamer 188 or Polysorbate 20,
wherein, when the formulation is reconstituted in water, pH is 6 to 8, for example 6.5 to 7.5, for example 7.

In a particular embodiment, the lyophilized formulation of the present disclosure is a composition resulting from lyophilizing a solution comprising, per vial, cartridge, or syringe:
10 mg to 80 mg of IL-31 antagonist;
0.8 mg to 4 mg of tris(hydroxymethyl)aminomethane;
8 mg to 40 mg of arginine;
30 mg to 110 mg of sucrose or trehalose; and
0.1 mg to 0.7 mg of Poloxamer 188 or Polysorbate 20,
wherein, when the formulation is reconstituted in water, pH is 6 to 8, for example 6.5 to 7.5, for example 7.

In one embodiment, the lyophilized formulation of the present disclosure is a composition resulting from lyophilizing a solution comprising:
61 mg/mL to 75 mg/mL, for example 68 mg/mL anti-IL-31RA neutralizing antibody;
11 mmol/L to 16 mmol/L, for example 13.6 mmol/L Tris-HCl;
82 mmol/L to 122 mmol/L, for example 102 mmol/L Arg-HCl;
153 mmol/L to 187 mmol/L, for example 170 mmol/L sucrose or trehalose; and
0.17 mg/mL to 0.51 mg/mL, for example 0.34 mg/mL Poloxamer 188 or Polysorbate 20,
wherein, when the formulation is reconstituted in water, pH is 6 to 8, for example 6.5 to 7.5, and for example 7.

In another embodiment, the lyophilized formulation of the present disclosure is a composition resulting from lyophilizing a solution comprising:
45 mg/mL to 55 mg/mL, for example 50 mg/mL anti-IL-31RA neutralizing antibody;
8 mmol/L to 12 mmol/L, for example 10 mmol/L Tris-HCl;
60 mmol/L to 90 mmol/L, for example 75 mmol/L Arg-HCl;
113 mmol/L to 138 mmol/L, for example 125 mmol/L sucrose or trehalose; and
0.13 mg/mL to 0.38 mg/mL, for example 0.25 mg/mL Poloxamer 188 or Polysorbate 20,
wherein, when the formulation is reconstituted in water, pH is 6 to 8, for example 6.5 to 7.5, and for example 7.

In still another embodiment, the lyophilized formulation of the present disclosure is a composition resulting from lyophilizing a solution comprising:
14 mg/mL to 17 mg/mL, for example 15 mg/mL anti-IL-31RA neutralizing antibody;
5 mmol/L to 7 mmol/L, for example 6 mmol/L Tris-HCl;
36 mmol/L to 54 mmol/L, for example 45 mmol/L Arg-HCl;
68 mmol/L to 83 mmol/L, for example 75 mmol/L sucrose or trehalose; and
0.08 mg/mL to 0.23 mg/mL, for example 0.15 mg/mL Poloxamer 188 or Polysorbate 20, wherein, when the formulation is reconstituted in water, pH is 6 to 8, for example 6.5 to 7.5, and for example 7.

In a further embodiment, the lyophilized formulation of the present disclosure is a composition resulting from lyophilizing a solution comprising:
7 mg/mL to 8 mg/mL, for example 7.5 mg/mL anti-IL-31RA neutralizing antibody;
5 mmol/L to 7 mmol/L, for example 6 mmol/L Tris-HCl;
36 mmol/L to 54 mmol/L, for example 45 mmol/L Arg-HCl;
68 mmol/L to 83 mmol/L, for example 75 mmol/L sucrose or trehalose; and
0.08 mg/mL to 0.23 mg/mL, for example 0.15 mg/mL Poloxamer 188 or Polysorbate 20,
wherein, when the formulation is reconstituted in water, pH is 6 to 8, for example 6.5 to 7.5, and for example 7.

The amount of each component contained in the lyophilized formulation of the present disclosure can also be represented as weight (mass) per container such as vial, cartridge, and syringe. A container may contain a single dose or multiple doses (for example, two doses, three doses, four doses, etc.) of the formulation. For example, a container contains a single dose of the formulation. Multiple containers may also be used for a single dose. The dose per administration may be appropriately determined according to the method of administration (e.g. subcutaneous administration), target disease (e.g. atopic dermatitis), purpose of use (e.g. for prevention or treatment), type of patient (e.g. adult or child), patient's conditions (e.g. severity of pruritus), and the like. In accordance with that, the amount of solvent such as water to be added to the container for reconstituting the lyophilized formulation can be appropriately determined. When the formulation is subcutaneously administered, the liquid volume for a single dose (in the case of the lyophilized formulation, the volume of liquid to be administered after reconstitution with water) may be, for example, 0.1 mL to 10 mL, 0.2 mL to 5 mL, 0.2 mL to 1.6 mL, 0.5 mL to 2 mL, 0.8 mL to 1.2 mL, or 0.9 mL to 1.1 mL, and for example, 1.0 mL, but is not limited thereto. It should be noted that those skilled in the art will naturally understand that a container may be overfilled with the formulation to ensure that an amount sufficient for administering a single dose or multiple doses of the IL-31 antagonist can be obtained from one container (such as vial, cartridge, or syringe), taking into account a loss of drug liquid when being administered.

In one embodiment, the lyophilized formulation of the present disclosure comprises, per container such as syringe:
68 mg to 83 mg, for example 75 mg of anti-IL-31RA neutralizing antibody (an anti-IL-31RA antibody comprising the H chain of SEQ ID NO: 9 and the L chain of SEQ ID NO: 10);
1.4 mg to 2.2 mg, for example 1.8 mg of tris(hydroxymethyl)aminomethane;
15 mg to 23 mg, for example 19 mg of arginine;
58 mg to 70 mg, for example 64 mg of sucrose; and
0.2 mg to 0.6 mg, for example 0.4 mg of Poloxamer 188.

In the above-mentioned embodiment, regarding the descriptions of numerical values, it is intended that a numerical value at the smallest digit (for example, ones place) includes values in which one place smaller than the smallest digit (for example, when the smallest digit is ones place, first decimal place) is rounded off. More specifically, the lyophilized formulation of the present disclosure can also be referred to as comprising, per container such as syringe:
75 mg (74.5 mg to 75.4 mg) of anti-IL-31RA neutralizing antibody (an anti-IL-31RA antibody comprising the H chain of SEQ ID NO: 9 and the L chain of SEQ ID NO: 10);
1.8 mg (1.75 mg to 1.84 mg) of tris(hydroxymethyl)aminomethane;
19 mg (18.5 mg to 19.4 mg) of arginine;
64 mg (63.5 mg to 64.4 mg) of sucrose; and
0.4 mg (0.35 mg to 0.44 mg) of Poloxamer 188.

Furthermore, in the above-mentioned embodiment, the weight of the above-mentioned tris(hydroxymethyl)aminomethane may be a sum of the weight of free tris(hydroxymethyl)aminomethane and the weight of tris(hydroxymethyl)aminomethane contained in tris(hydroxymethyl)aminomethane hydrochloride (which may be added as a pH adjuster). In addition, the above-mentioned arginine may be added as a salt containing arginine (e.g., arginine hydrochloride). Those skilled in the art will understand that when a salt containing arginine is added, the weight of the above-mentioned arginine is the weight of arginine contained in the salt.

Accordingly, the lyophilized formulation of the present disclosure can also be referred to as comprising, per container such as syringe:
75 mg of anti-IL-31RA neutralizing antibody (an anti-IL-31RA antibody comprising the H chain of SEQ ID NO: 9 and the L chain of SEQ ID NO: 10);
0.24 mg of tris(hydroxymethyl)aminomethane;
23.6 mg of L-arginine hydrochloride;
63.9 mg of sucrose;
0.37 mg of Poloxamer 188; and
tris(hydroxymethyl)aminomethane hydrochloride as a pH adjuster.

In another embodiment, the lyophilized formulation of the present disclosure comprises, per container such as syringe:
35 mg to 43 mg, for example 39 mg of anti-IL-31RA neutralizing antibody (an anti-IL-31RA antibody comprising the H chain of SEQ ID NO: 9 and the L chain of SEQ ID NO: 10);
0.7 mg to 1.1 mg, for example 0.9 mg of tris(hydroxymethyl)aminomethane;
8 mg to 12 mg, for example 10 mg of arginine;
30 mg to 36 mg, for example 33 mg of sucrose; and
0.1 mg to 0.3 mg, for example 0.2 mg of Poloxamer 188.

In the above-mentioned embodiment, regarding the descriptions of numerical values, it is intended that a numerical value at the smallest digit (for example, ones place) includes values in which one place smaller than the smallest digit (for example, when the smallest digit is ones place, first decimal place) is rounded off. More specifically, the lyophilized formulation of the present disclosure can also be referred to as comprising, per container such as syringe:
39 mg (38.5 mg to 39.4 mg) of anti-IL-31RA neutralizing antibody (an anti-IL-31RA antibody comprising the H chain of SEQ ID NO: 9 and the L chain of SEQ ID NO: 10);
0.9 mg (0.85 mg to 0.94 mg) of tris(hydroxymethyl)aminomethane;
10 mg (9.5 mg to 10.4 mg) of arginine;
33 mg (32.5 mg to 33.4 mg) of sucrose; and
0.2 mg (0.15 mg to 0.24 mg) of Poloxamer 188.

In a further embodiment, the lyophilized formulation of the present disclosure comprises, per container such as cartridge:

32 mg to 40 mg, for example 36 mg of anti-IL-31RA neutralizing antibody (an anti-IL-31RA antibody comprising the H chain of SEQ ID NO: 9 and the L chain of SEQ ID NO: 10);
0.7 mg to 1.1 mg, for example 0.9 mg of tris(hydroxymethyl)aminomethane;
7 mg to 11 mg, for example 9 mg of arginine;
28 mg to 34 mg, for example 31 mg of sucrose; and
0.1 mg to 0.3 mg, for example 0.2 mg of Poloxamer 188.

In the above-mentioned embodiment, regarding the descriptions of numerical values, it is intended that a numerical value at the smallest digit (for example, ones place) includes values in which one place smaller than the smallest digit (for example, when the smallest digit is ones place, first decimal place) is rounded off. More specifically, the lyophilized formulation of the present disclosure can also be referred to as comprising, per container such as cartridge:
36 mg (35.5 mg to 36.4 mg) of anti-IL-31RA neutralizing antibody (an anti-IL-31RA antibody comprising the H chain of SEQ ID NO: 9 and the L chain of SEQ ID NO: 10);
0.9 mg (0.85 mg to 0.94 mg) of tris(hydroxymethyl)aminomethane;
9 mg (8.5 mg to 9.4 mg) of arginine;
31 mg (30.5 mg to 31.4 mg) of sucrose; and
0.2 mg (0.15 mg to 0.24 mg) of Poloxamer 188.

In still another embodiment, the lyophilized formulation of the present disclosure comprises, per container such as vial:
46 mg to 56 mg, for example 51 mg of anti-IL-31RA neutralizing antibody (an anti-IL-31RA antibody comprising the H chain of SEQ ID NO: 9 and the L chain of SEQ ID NO: 10);
2.0 mg to 3.0 mg, for example 2.5 mg of tris(hydroxymethyl)aminomethane;
22 mg to 32 mg, for example 27 mg of arginine;
79 mg to 97 mg, for example 88 mg of sucrose; and
0.3 mg to 0.8 mg, for example 0.5 mg of Poloxamer 188.

In the above-mentioned embodiment, regarding the descriptions of numerical values, it is intended that a numerical value at the smallest digit (for example, ones place) includes values in which one place smaller than the smallest digit (for example, when the smallest digit is ones place, first decimal place) is rounded off. More specifically, the lyophilized formulation of the present disclosure can also be referred to as comprising, per container such as vial:
51 mg (50.5 mg to 51.4 mg) of anti-IL-31RA neutralizing antibody (an anti-IL-31RA antibody comprising the H chain of SEQ ID NO: 9 and the L chain of SEQ ID NO: 10);
2.5 mg (2.45 mg to 2.54 mg) of tris(hydroxymethyl)aminomethane;
27 mg (26.5 mg to 27.4 mg) of arginine;
88 mg (87.5 mg to 88.4 mg) of sucrose; and
0.5 mg (0.45 mg to 0.54 mg) of Poloxamer 188.

Furthermore, in another embodiment, the lyophilized formulation of the present disclosure comprises, per container such as vial:
27 mg to 33 mg, for example 30 mg of anti-IL-31RA neutralizing antibody (an anti-IL-31RA antibody comprising the H chain of SEQ ID NO: 9 and the L chain of SEQ ID NO: 10);
2.4 mg to 3.6 mg, for example 3.0 mg of tris(hydroxymethyl)aminomethane;
26 mg to 38 mg, for example 32 mg of arginine;
94 mg to 114 mg, for example 104 mg of sucrose; and
0.3 mg to 0.9 mg, for example 0.6 mg of Poloxamer 188.

In the above-mentioned embodiment, regarding the descriptions of numerical values, it is intended that a numerical value at the smallest digit (for example, ones place) includes values in which one place smaller than the smallest digit (for example, when the smallest digit is ones place, first decimal place) is rounded off. More specifically, the lyophilized formulation of the present disclosure can also be referred to as comprising, per container such as vial:
30 mg (29.5 mg to 30.4 mg) of anti-IL-31RA neutralizing antibody (an anti-IL-31RA antibody comprising the H chain of SEQ ID NO: 9 and the L chain of SEQ ID NO: 10);
3.0 mg (2.95 mg to 3.04 mg) of tris(hydroxymethyl)aminomethane;
32 mg (31.5 mg to 32.4 mg) of arginine;
104 mg (103.5 mg to 104.4 mg) of sucrose; and
0.6 mg (0.55 mg to 0.64 mg) of Poloxamer 188.

In a still another embodiment, the lyophilized formulation of the present disclosure comprises, per container such as vial:
17 mg to 21 mg, for example 19 mg of anti-IL-31RA neutralizing antibody (an anti-IL-31RA antibody comprising the H chain of SEQ ID NO: 9 and the L chain of SEQ ID NO: 10);
1.5 mg to 2.3 mg, for example 1.9 mg of tris(hydroxymethyl)aminomethane;
16 mg to 24 mg, for example 20 mg of arginine;
59 mg to 73 mg, for example 66 mg of sucrose; and
0.2 mg to 0.6 mg, for example 0.4 mg of Poloxamer 188.

In the above-mentioned embodiment, regarding the descriptions of numerical values, it is intended that a numerical value at the smallest digit (for example, ones place) includes values in which one place smaller than the smallest digit (for example, when the smallest digit is ones place, first decimal place) is rounded off. More specifically, the lyophilized formulation of the present disclosure can also be referred to as comprising, per container such as vial:
19 mg (18.5 mg to 19.4 mg) of anti-IL-31RA neutralizing antibody (an anti-IL-31RA antibody comprising the H chain of SEQ ID NO: 9 and the L chain of SEQ ID NO: 10);
1.9 mg (1.85 mg to 1.94 mg) of tris(hydroxymethyl)aminomethane;
20 mg (19.5 mg to 20.4 mg) of arginine;
66 mg (65.5 mg to 66.4 mg) of sucrose; and
0.4 mg (0.35 mg to 0.44 mg) of Poloxamer 188.

In a further embodiment, the lyophilized formulation of the present disclosure comprises, per container such as vial:
13 mg to 15 mg, for example 14 mg of anti-IL-31RA neutralizing antibody (an anti-IL-31RA antibody comprising the H chain of SEQ ID NO: 9 and the L chain of SEQ ID NO: 10);
1.0 mg to 1.6 mg, for example 1.3 mg of tris(hydroxymethyl)aminomethane;
12 mg to 18 mg, for example 15 mg of arginine;
42 mg to 52 mg, for example 47 mg of sucrose; and
0.2 mg to 0.5 mg, for example 0.3 mg of Poloxamer 188.

In the above-mentioned embodiment, regarding the descriptions of numerical values, it is intended that a numerical value at the smallest digit (for example, ones place) includes values in which one place smaller than the smallest digit (for example, when the smallest digit is ones place, first decimal place) is rounded off. More specifically, the lyophilized formulation of the present disclosure can also be referred to as comprising, per container such as vial:

14 mg (13.5 mg to 14.4 mg) of anti-IL-31RA neutralizing antibody (an anti-IL-31RA antibody comprising the H chain of SEQ ID NO: 9 and the L chain of SEQ ID NO: 10);
1.3 mg (1.25 mg to 1.34 mg) of tris(hydroxymethyl)aminomethane;
15 mg (14.5 mg to 15.4 mg) of arginine;
47 mg (46.5 mg to 47.4 mg) of sucrose; and
0.3 mg (0.25 mg to 0.34 mg) of Poloxamer 188.

In one embodiment, regarding the lyophilized formulation of the present disclosure, when the formulation is reconstituted in water, the reconstituted solution comprises:

90 mg/mL to 110 mg/mL, for example 100 mg/mL anti-IL-31RA neutralizing antibody (an anti-IL-31RA antibody comprising the H chain of SEQ ID NO: 9 and the L chain of SEQ ID NO: 10);
16 mmol/L to 24 mmol/L, for example 20 mmol/L Tris-HCl;
120 mmol/L to 180 mmol/L, for example 150 mmol/L Arg-HCl;
225 mmol/L to 275 mmol/L, for example 250 mmol/L sucrose or trehalose; and
0.25 mg/mL to 0.75 mg/mL, for example 0.50 mg/mL Poloxamer 188 or Polysorbate 20,
where pH is 6 to 8, for example 6.7 to 7.3, and for example 7.

In another embodiment, regarding the lyophilized formulation of the present disclosure, when the formulation is reconstituted in water, the reconstituted solution comprises:

55 mg/mL to 68 mg/mL, for example 61.5 mg/mL anti-IL-31RA neutralizing antibody (an anti-IL-31RA antibody comprising the H chain of SEQ ID NO: 9 and the L chain of SEQ ID NO: 10);
10 mmol/L to 15 mmol/L, for example 12.3 mmol/L Tris-HCl;
74 mmol/L to 110 mmol/L, for example 92 mmol/L Arg-HCl;
139 mmol/L to 169 mmol/L, for example 154 mmol/L sucrose or trehalose; and
0.16 mg/mL to 0.47 mg/mL, for example 0.31 mg/mL Poloxamer 188 or Polysorbate20,
where pH is 6 to 8, for example 6.7 to 7.3, and for example 7.

Furthermore, in another embodiment, regarding the lyophilized formulation of the present disclosure, when the formulation is reconstituted in water, the reconstituted solution comprises:

45 mg/mL to 55 mg/mL, for example 50 mg/mL anti-IL-31RA neutralizing antibody (an anti-IL-31RA antibody comprising the H chain of SEQ ID NO: 9 and the L chain of SEQ ID NO: 10);
16 mmol/L to 24 mmol/L, for example 20 mmol/L Tris-HCl;
120 mmol/L to 180 mmol/L, for example 150 mmol/L Arg-HCl;
225 mmol/L to 275 mmol/L, for example 250 mmol/L sucrose or trehalose; and
0.25 mg/mL to 0.75 mg/mL, for example 0.50 mg/mL Poloxamer 188 or Polysorbate 20,
where pH is 6 to 8, for example 6.7 to 7.3, and for example 7.

In still another embodiment, regarding the lyophilized formulation of the present disclosure, when the formulation is reconstituted in water, the reconstituted solution comprises:

23 mg/mL to 28 mg/mL, for example 25 mg/mL anti-IL-31RA neutralizing antibody (anti-IL-31RA antibody comprising the H chain of SEQ ID NO: 9 and the L chain of SEQ ID NO: 10);
16 mmol/L to 24 mmol/L, for example 20 mmol/L Tris-HCl;
120 mmol/L to 180 mmol/L, for example 150 mmol/L Arg-HCl;
225 mmol/L to 275 mmol/L, for example 250 mmol/L sucrose or trehalose; and
0.25 mg/mL to 0.75 mg/mL, for example 0.50 mg/mL Poloxamer 188 or Polysorbate 20,
where pH is 6 to 8, for example 6.7 to 7.3, and for example 7.

Exemplary embodiments of the formulation of the present disclosure include, but are not limited to, the following formulations:

[Example of the Formulation of the Present Disclosure (the Weight of Each Component)]

|  | Formulation per container such as syringe | | | Formulation per container such as cartridge | | | Formulation per container such as syringe | | |
| --- | --- | --- | --- | --- | --- | --- | --- | --- | --- |
|  | Target | Minimum | Maximum | Target | Minimum | Maximum | Target | Minimum | Maximum |
| Anti-IL-31RA neutralizing antibody | 39 mg | 35 mg | 43 mg | 36 mg | 32 mg | 40 mg | 75 mg | 68 mg | 83 mg |
| Tris (hydroxymethyl) aminomethane | 0.9 mg | 0.7 mg | 1.1 mg | 0.9 mg | 0.7 mg | 1.1 mg | 1.8 mg | 1.4 mg | 2.2 mg |
| Arginine | 10 mg | 8 mg | 12 mg | 9 mg | 7 mg | 11 mg | 19 mg | 15 mg | 23 mg |
| Sucrose | 33 mg | 30 mg | 36 mg | 31 mg | 28 mg | 34 mg | 64 mg | 58 mg | 70 mg |
| Poloxamer 188 | 0.2 mg | 0.1 mg | 0.3 mg | 0.2 mg | 0.1 mg | 0.3 mg | 0.4 mg | 0.2 mg | 0.6 mg |

|  | Formulation per container such as vial | | | Formulation per container such as vial | | | Formulation per container such as vial | | | Formulation per container such as vial | | |
| --- | --- | --- | --- | --- | --- | --- | --- | --- | --- | --- | --- | --- |
|  | Target | Minimum | Maximum | Target | Minimum | Maximum | Target | Minimum | Maximum | Target | Minimum | Maximum |
| Anti-IL-31RA neutralizing antibody | 30 mg | 27 mg | 33 mg | 19 mg | 17 mg | 21 mg | 14 mg | 13 mg | 15 mg | 51 mg | 46 mg | 56 mg |

-continued

| | | | | | | | | | | | | |
|---|---|---|---|---|---|---|---|---|---|---|---|---|
| Tris (hydroxymethyl) aminomethane | 3.0 mg | 2.4 mg | 3.6 mg | 1.9 mg | 1.5 mg | 2.3 mg | 1.3 mg | 1.0 mg | 1.6 mg | 2.5 mg | 2.0 mg | 3.0 mg |
| Arginine | 32 mg | 26 mg | 38 mg | 20 mg | 16 mg | 24 mg | 15 mg | 12 mg | 18 mg | 27 mg | 22 mg | 32 mg |
| Sucrose | 104 mg | 94 mg | 114 mg | 66 mg | 59 mg | 73 mg | 47 mg | 42 mg | 52 mg | 88 mg | 79 mg | 97 mg |
| Poloxamer 188 | 0.6 mg | 0.3 mg | 0.9 mg | 0.4 mg | 0.2 mg | 0.6 mg | 0.3 mg | 0.2 mg | 0.5 mg | 0.5 mg | 0.3 mg | 0.8 mg |

[Example of the Formulation of the Present Disclosure (the Concentration of Each Component in the Solution Prior to Lyophilization)]

| | Formulation of solution prior to lyophilization | | | Formulation of solution prior to lyophilization | | |
|---|---|---|---|---|---|---|
| | Target | Minimum | Maximum | Target | Minimum | Maximum |
| Anti-IL-31RA neutralizing antibody | 50 mg/mL | 45 mg/mL | 55 mg/mL | 68 mg/mL | 61 mg/mL | 75 mg/mL |
| Tris-HCl or tris(hydroxymethyl)aminomethane | 10 mmol/L | 8 mmol/L | 12 mmol/L | 13.6 mmol/L | 11 mmol/L | 16 mmol/L |
| Arg-HCl or arginine | 75 mmol/L | 60 mmol/L | 90 mmol/L | 102 mmol/L | 82 mmol/L | 122 mmol/L |
| Sucrose or trehalose | 125 mmol/L | 113 mmol/L | 138 mmol/L | 170 mmol/L | 153 mmol/L | 187 mmol/L |
| Poloxamer 188 or Polysorbate 20 | 0.25 mg/mL | 0.13 mg/mL | 0.38 mg/mL | 0.34 mg/mL | 0.17 mg/mL | 0.51 mg/mL |

| | Formulation of solution prior to lyophilization | | | Formulation of solution prior to lyophilization | | |
|---|---|---|---|---|---|---|
| | Target | Minimum | Maximum | Target | Minimum | Maximum |
| Anti-IL-31RA neutralizing antibody | 7.5 mg/mL | 7 mg/mL | 8 mg/mL | 15 mg/mL | 14 mg/mL | 17 mg/mL |
| Tris-HCl or tris(hydroxymethyl)aminomethane | 6 mmol/L | 5 mmol/L | 7 mmol/L | 6 mmol/L | 5 mmol/L | 7 mmol/L |
| Arg-HCl or arginine | 45 mmol/L | 36 mmol/L | 54 mmol/L | 45 mmol/L | 36 mmol/L | 54 mmol/L |
| Sucrose or trehalose | 75 mmol/L | 68 mmol/L | 83 mmol/L | 75 mmol/L | 68 mmol/L | 83 mmol/L |
| Poloxamer 188 or Polysorbate 20 | 0.15 mg/mL | 0.08 mg/mL | 0.23 mg/mL | 0.15 mg/mL | 0.08 mg/mL | 0.23 mg/mL |

[Example of the Formulation of the Present Disclosure (the Concentration of Each Component in the Reconstituted Solution)]

| | Formulation of reconstituted solution | | | Formulation of reconstituted solution | | |
|---|---|---|---|---|---|---|
| | Target | Minimum | Maximum | Target | Minimum | Maximum |
| Anti-IL-31RA neutralizing antibody | 61.5 mg/mL | 55 mg/mL | 68 mg/mL | 100 mg/mL | 90 mg/mL | 110 mg/mL |
| Tris-HCl or tris(hydroxymethyl)aminomethane | 12.3 mmol/L | 10 mmol/L | 15 mmol/L | 20 mmol/L | 16 mmol/L | 24 mmol/L |
| Arg-HCl or arginine | 92 mmol/L | 74 mmol/L | 110 mmol/L | 150 mmol/L | 120 mmol/L | 180 mmol/L |
| Sucrose or trehalose | 154 mmol/L | 139 mmol/L | 169 mmol/L | 250 mmol/L | 225 mmol/L | 275 mmol/L |
| Poloxamer 188 or Polysorbate 20 | 0.31 mg/mL | 0.16 mg/mL | 0.47 mg/mL | 0.50 mg/mL | 0.25 mg/mL | 0.75 mg/mL |

| | Formulation of reconstituted solution | | | Formulation of reconstituted solution | | |
|---|---|---|---|---|---|---|
| | Target | Minimum | Maximum | Target | Minimum | Maximum |
| Anti-IL-31RA neutralizing antibody | 25 mg/mL | 23 mg/mL | 28 mg/mL | 50 mg/mL | 45 mg/mL | 55 mg/mL |
| Tris-HCl or tris(hydroxymethyl)aminomethane | 20 mmol/L | 6 mmol/L | 24 mmol/L | 20 mmol/L | 16 mmol/L | 24 mmol/L |
| Arg-HCl or arginine | 150 mmol/L | 120 mmol/L | 180 mmol/L | 150 mmol/L | 120 mmol/L | 180 mmol/L |
| Sucrose or trehalose | 250 mmol/L | 225 mmol/L | 275 mmol/L | 250 mmol/L | 225 mmol/L | 275 mmol/L |
| Poloxamer 188 or Polysorbate 20 | 0.50 mg/mL | 0.25 mg/mL | 0.75 mg/mL | 0.50 mg/mL | 0.25 mg/mL | 0.75 mg/mL |

In a non-limiting embodiment, the formulations of the present disclosure can be used for preventing and/or treating IL-31-associated disorders or symptoms accompanying therewith. In one embodiment, IL-31-associated disorders are inflammatory disorders associated with IL-31 signaling. In a particular embodiment, IL-31-associated disorders are atopic dermatitis, pruritus (e.g., dialytic pruritus or pruritus caused by atopic dermatitis), or prurigo nodularis. In another particular embodiment, the treatment of IL-31-associated disorders or symptoms accompanying therewith is the improvement of sleep disturbance induced by pruritus (e.g., increase in the time from falling asleep to awakening and/or a decrease in sleep onset latency (the time from going to bed to falling asleep)). In another embodiment, the treatment of IL-31-associated disorders or symptoms accompanying therewith is the suppression of at least one symptom caused by atopic dermatitis selected from the group consisting of redness, induration, papules, edema, excoriations, and lichenification. In a particular embodiment, atopic dermatitis is moderate or severe atopic dermatitis for which topical therapy (e.g., treatment by topical steroids or topical calcineurin inhibitors) is not sufficiently effective or is intolerable. In one embodiment, the formulations of the present disclosure are formulations for parental administration, for example, for intravenous administration or for subcutaneous administration.

In a non-limiting embodiment, the present disclosure relates to a method for stabilizing an antibody in an antibody-containing formulation, the method comprising preparing an antibody-containing solution comprising arginine and/or a salt thereof, and/or sucrose and/or trehalose, wherein the molar ratio of arginine and/or a salt thereof to antibody in the solution is 220:1 to 1100:1 and the molar ratio of sucrose or trehalose to the antibody is 370:1 to 1840:1. In another non-limiting embodiment, the present disclosure relates to a method for suppressing antibody aggregation (aggregate formation) in an antibody-containing formulation, the method comprising preparing an antibody-containing lyophilized formulation by freeze-drying an antibody-containing solution comprising 45 mmol/L to 150 mmol/L arginine-hydrochloride (Arg-HCl) and 75 mmol/L to 250 mmol/L sucrose or trehalose. In a further non-limiting embodiment, the present disclosure relates to a method for reducing components with charge heterogeneity in an antibody-containing lyophilized formulation, the method comprising preparing an antibody-containing lyophilized formulation by freeze-drying an antibody-containing solution comprising 45 mmol/L to 150 mmol/L arginine-hydrochloride (Arg-HCl) and 75 mmol/L to 250 mmol/L sucrose or trehalose. In one embodiment, an antibody-containing solution before lyophilization further comprises 6 mmol/L to 20 mmol/L tris(hydroxymethyl)aminomethane-hydrochloride and 0.15 mg/mL to 0.50 mg/mL Poloxamer 188.

In a non-limiting embodiment, the present disclosure relates to a method for preventing and/or treating IL-31-associated disorders, comprising administering an IL-31 antagonist to a subject affected with IL-31-associated disorders or at a risk of being affected with IL-31-associated disorders, the method comprising preparing a lyophilized formulation by freeze-drying a solution comprising 6 mg/mL to 100 mg/mL IL-31 antagonist, 45 mmol/L to 150 mmol/L arginine-hydrochloride (Arg-HCl), and 75 mmol/L to 250 mmol/L sucrose or trehalose; preparing a reconstituted solution by reconstituting the lyophilized formulation; and administering the reconstituted solution to the subject.

In a non-limiting embodiment, the present disclosure relates to use of an IL-31 antagonist in the manufacture of a medicament for prevention and/or treatment of IL-31-associated disorders, characterized in that a lyophilized formulation is prepared by freeze-drying a solution comprising 6 mg/mL to 100 mg/mL IL-31 antagonist, 45 mmol/L to 150 mmol/L arginine-hydrochloride (Arg-HCl), and 75 mmol/L to 250 mmol/L sucrose or trehalose.

In a non-limiting embodiment, the present disclosure relates to an IL-31 antagonist for use in the prevention and/or treatment of IL-31-associated disorders, characterized in that a lyophilized formulation resulting from lyophilizing a solution comprising 6 mg/mL to 100 mg/mL IL-31 antagonist, 45 mmol/L to 150 mmol/L arginine-hydrochloride (Arg-HCl), and 75 mmol/L to 250 mmol/L sucrose or trehalose is reconstituted and used.

In one embodiment, the above-mentioned solution before lyophilization may further comprise 6 mmol/L to 20 mmol/L tris(hydroxymethyl)aminomethane-hydrochloride and 0.15 mg/mL to 0.50 mg/mL Poloxamer 188.

In a non-limiting embodiment, the present disclosure relates to formulations for injection or kits comprising (i) a container; (ii) a lyophilized formulation of the present disclosure; and (iii) optionally water for injection for reconstituting the lyophilized formulation. In one embodiment, a container of the formulations for injection or kits of the present disclosure is a glass syringe, a glass cartridge or a glass vial. In a particular embodiment, the container of formulations for injection or kits of the present disclosure is a dual chamber syringe (DCS) or dual chamber cartridge (DCC), and a lyophilized formulation and water for injection are enclosed in separate compartments in the container, i.e., the lyophilized formulation of the present disclosure is filled into either one of two chambers and water for injection is filled into the other chamber. Preferably, water for injection is water, and optionally satisfies the standards of "water for injection" specified in the Pharmacopoeia of Japan.

IL-31 (interleukin-31) is a T-cell cytokine. It is known that IL-31 is involved in pruritus, and in transgenic mice overexpressing IL-31, dermatitis-like symptoms similar to atopic dermatitis occur, and persistent scratching behavior is observed.

The nucleic acid sequence and amino acid sequence of human IL-31 are also known as RefSeq accession number NM_001014336 and RefSeq accession number NP_001014358, respectively.

The receptor for IL-31 is formed of a heterodimer of IL-31 receptor A (IL-31RA) and oncostatin M receptor (OSMR) (Nat Immunol (2004) 5, 752-60). IL-31RA, also referred to as NR10, is known to have a plurality of splicing variants (WO 00/075314). Known splicing variants are NR10.1 (652 amino acids), NR10.2 (252 amino acids), NR10.3 (662 amino acids, also referred to as IL-31RAv4), IL31RAv3 (764 amino acids), and such and examples of preferred IL-31RA include NR10.3 (IL-31RAv4) and IL-31RAv3. The nucleic acid sequence and amino acid sequence of human IL-31RA (IL-31RAv4) are also known as RefSeq accession number NM_001242638 and RefSeq accession number NP_001229567, respectively. The nucleic acid sequence and the amino acid sequence of human IL-31RA (IL-31RAv3) are also known as RefSeq accession number NM_139017 and RefSeq accession number NP_620586, respectively. The nucleic acid sequence and the amino acid sequence of human OSMR are also known as RefSeq accession number NM_003999 and RefSeq accession number NP_003990, respectively.

The IL-31 antagonist in the present disclosure, in one embodiment, refers to a compound that suppresses or blocks IL-31-induced intracellular signaling. This compound can also be expressed as a compound that inhibits IL-31 signaling. Such a compound may be a naturally occurring compound or an artificially synthesized compound. Moreover, such a compound may be a low-molecular-weight compound or a high-molecular-weight compound such as a protein.

It is known that IL-31 that is present extracellularly triggers intracellular signaling via the IL-31 receptor (heterodimer of IL-31RA and OSMR) present on the cell surface (Nat Immunol (2004) 5, 752-760). The extracellular domain of the IL-31 receptor includes an IL-31-binding domain, and binding of IL-31 thereto causes a change in the conformation of the IL-31 receptor. As a result, intracellular signaling is initiated from the intracellular domain of the IL-31 receptor.

In one method, whether a certain compound inhibits IL-31 signaling can be verified by examining whether the compound inhibits binding of IL-31 to the IL-31 receptor. Examples of methods for making such a determination include an assay using ELISA or flow cytometry and an assay using surface plasmon resonance. With ELISA, for example, whether the compound inhibits the binding of IL-31 to the IL-31 receptor can be evaluated by immobilizing the IL-31 receptor (or IL-31RA) protein onto a plate, preparing a system for detecting the amount of IL-31 protein that binds thereto through the use of a secondary antibody such as an enzyme-labeled anti-IL-31 antibody, and determining whether or not the addition of the compound reduces the amount of detected IL-31 protein.

In an alternative method, whether a certain compound inhibits IL-31 signaling can be verified by examining whether the bioactivity induced by the action of IL-31 on cells is inhibited by the compound. The bioactivity is not particularly limited as long as it can be quantitatively or qualitatively determined using any method, and examples of such bioactivities include cell proliferative activity, protein phosphorylation activity, and gene/protein expression-inducing activity. For example, whether the compound inhibits IL-31 signaling can be evaluated by preparing cells that express the IL-31 receptor on the surface, and whose proliferative activity is induced in response to external IL-31 stimulation, and determining whether or not the addition of the compound reduces the IL-31-induced cell proliferative activity. As such cells, naturally occurring cells inherently expressing the IL-31 receptor may be used, or recombinant cells artificially synthesized to express the IL-31 receptor may be used. A suitable example of recombinant cells includes Ba/F3 cells expressing the IL-31 receptor. As a further alternative, the method described in the document of Dillon et al. (Nat Immunol (2004) 5, 752-760) may be used.

In the present disclosure, the degree of inhibition of IL-31 signaling by the IL-31 antagonist may be, but not limited to, at least 10% or more, preferably 20% or more, 30% or more, 40% or more, 50% or more, 60% or more, 70% or more, and 80% or more, and particularly preferably 90% or more, 95% or more, and 98% or more.

In the present disclosure, a preferred embodiment of the compound that inhibits IL-31 signaling includes a protein that inhibits IL-31 signaling. The protein used herein is not particularly limited as long as it has the property of specifically binding to IL-31 or the IL-31 receptor. Examples of preferred proteins include antibodies and antibody-like molecules (Curr Opin Biotechnol (2006) 17, 653-658; Curr Opin Struct Biol (1997) 7, 463-469; and Protein Sci (2006) 15, 14-27). Antibodies include any antibodies such as monoclonal antibodies (e.g., IgG, IgM, IgE, IgA, and IgD), polyclonal antibodies, engineered antibodies (e.g., chimeric antibodies, humanized antibodies, and glycoengineered antibodies (WO 99/54342 and WO 00/61739)), antibody fragments (e.g., Fab, F(ab')2, Fv, and CDR), multi-specific antibodies (e.g., bispecific antibodies), and conjugated antibodies (e.g., antibodies conjugated with polyethylene glycol (PEG), radioactive isotopes, or drugs). On the other hand, examples of antibody-like molecules include DARPin (WO 2002/020565), Affibody (WO 1995/001937), Avimer (WO 2004/044011), and Adnectin (WO 2002/032925). More preferred is an antibody that inhibits IL-31 signaling. Examples of other preferred proteins that inhibit IL-31 signaling include a protein containing the extracellular domain of IL-31RA and a protein containing each extracellular domain of the IL-31 receptor (heterodimer of IL-31RA and OSMR).

In the present disclosure, preferred embodiments of the antibody that inhibits IL-31 signaling include an antibody that inhibits IL-31 signaling by binding to IL-31 (anti-IL-31 neutralizing antibody) and an antibody that inhibits IL-31 signaling by binding to the IL-31 receptor (anti-IL-31 receptor neutralizing antibody). Anti-IL-31 receptor neutralizing antibodies include an antibody that inhibits IL-31 signaling by binding to IL-31RA (anti-IL-31RA neutralizing antibody), an antibody that inhibits IL-31 signaling by binding to OSMR (anti-OSMR neutralizing antibody), and an antibody that inhibits IL-31 signaling by binding to the heterodimer of IL-31RA and OSMR (anti-IL-31RA/OSMR heterodimer neutralizing antibody). Of these anti-IL-31 receptor neutralizing antibodies, preferred is an anti-IL-31RA neutralizing antibody or anti-IL-31RA/OSMR heterodimer neutralizing antibody, and more preferred is an anti-IL-31RA neutralizing antibody.

Antibodies used in the present invention are not particularly limited so long as they bind to a desired antigen to inhibit IL-31 signaling, and they may be polyclonal or monoclonal antibodies. Monoclonal antibodies are preferred in that homogeneous antibodies can be stably produced.

Amino acids contained in the amino acid sequences of the present invention may be post-translationally modified (for example, the modification of an N-terminal glutamine into a pyroglutamic acid by pyroglutamylation is well-known to those skilled in the art). Naturally, such post-translationally modified amino acids are included in the antibodies used in the present invention.

The antibody that inhibits IL-31 signaling of the present disclosure in a further embodiment or another embodiment preferably comprises an amino acid variant of an H chain constant region sequence of IgG2, where the amino acid variant comprises glutamic acid at position 419 (EU numbering) in the H chain constant region sequence (SEQ ID NO: 12) of wild-type IgG2. This engineered antibody is advantageous in that it exhibits an increased plasma half-life, compared to a reference antibody comprising an H chain constant region sequence of wild-type IgG2 having the same amino acid sequence except for the amino acid variation at position 419. It is thought that such an increased plasma half-life was caused by a decrease in isoelectric point (pI) induced by the amino acid substitution with glutamic acid at position 419 (Example 2 of WO 2016/167263).

Thus, the lyophilized formulation and solution formulation of the present disclosure in one embodiment is advantageous in that it relates to a lyophilized formulation and solution formulation for providing an increased plasma half-life, compared to a (reference) lyophilized formulation and solution formulation comprising a reference antibody comprising an H chain constant region sequence of wild-type IgG2 having the same amino acid sequence except for the amino acid variation at position 419.

In this case, the antibody that inhibits IL-31 signaling of the present disclosure in a preferred embodiment is any of the following anti-IL-31RA neutralizing antibodies:

(1) an anti-IL-31RA antibody comprising an H chain variable region comprising CDR1 as set forth in SEQ ID NO: 1, CDR2 as set forth in SEQ ID NO: 2, and CDR3 as set forth in SEQ ID NO: 3, and an L chain variable region comprising CDR1 as set forth in SEQ ID NO: 4, CDR2 as set forth in SEQ ID NO: 5, and CDR3 as set forth in SEQ ID NO: 6;

(2) an anti-IL-31RA antibody comprising an H chain variable region as set forth in SEQ ID NO: 7 and an L chain variable region as set forth in SEQ ID NO: 8; and (3) an anti-IL-31RA antibody comprising an H chain as set forth in SEQ ID NO: 9 and an L chain as set forth in SEQ ID NO: 10.

It is understood that isoelectric point (pI), also simply referred to as "pI", may be either a theoretical isoelectric point or an experimentally measured isoelectric point, where it is not expressly described in the present specification, and unless it is contradictory in the context.

For example, the value of isoelectric point can be measured by isoelectric focusing known to those skilled in the art. The value of theoretical isoelectric point can be calculated using gene and amino acid sequence analysis software (e.g., Genetyx). Alternatively, the value of theoretical isoelectric point can be measured by performing a pharmacokinetic study of the antibody using, for example, the plasma of mice, rats, rabbits, dogs, monkeys, humans, or the like, in combination with a method known to those skilled in the art such as BIACORE, cell proliferation assay, ELISA, EIA (enzyme immunoassay), RIA (radioimmunoassay), or immunofluorescence.

Whether the plasma half-life of the antibody has changed before and after the amino acid variation (modification) may be verified by performing a pharmacokinetic study of the antibody using a method known to those skilled in the art, using, for example, the plasma of mice, rats, rabbits, dogs, monkeys, humans, or the like.

The antibody that inhibits IL-31 signaling of the present disclosure, in a still further embodiment or another embodiment, preferably does not (substantially) exhibit cross-reactivity with IL-31RA from any of mouse, rat, and rabbit, although it has cross-reactivity with IL-31RA from humans and cynomolgus monkeys.

Methods for preparing antibodies are well known to those skilled in the art, and antibodies can be prepared using the hybridoma method (Nature (1975) 256, 495) or the phage antibody library method (Nature (1991) 352, 624-628; J Mol Biol (1991) 222, 581-597), for example. Using the IL-31 protein or IL-31 receptor protein as an immunogen, a large number of anti-IL-31 antibodies or anti-IL-31 receptor antibodies can be obtained by these methods. Furthermore, screening of these antibodies using any of the above-described methods for detecting the compound that inhibits IL-31 signaling allows an anti-IL-31 neutralizing antibody or an anti-IL-31 receptor neutralizing antibody to be obtained. A protein such as IL-31 or the IL-31 receptor may also be prepared using a genetic engineering technology known to those skilled in the art. Specifically, such a protein can be prepared by inserting a gene encoding a desired protein into an expression vector, introducing the vector into an appropriate host cell, and then purifying the target protein expressed in the host cell or in the culture supernatant of the host cell.

Examples of preferred anti-IL-31 neutralizing antibodies include the anti-IL-31 antibodies described in WO 2006/122079, WO 2008/028192, and WO 2009/071696.

Examples of preferred anti-IL-31RA neutralizing antibodies include, but are not limited to, the anti-IL-31RA (NR10) antibody described in WO 2007/142325, the anti-IL-31RA (NR10) antibody described in WO 2009/072604, and the anti-IL-31RA (NR10) antibody described in WO 2010/064697.

Moreover, examples of other preferred anti-IL-31RA neutralizing antibodies include anti-human IL-31RA (neutralizing) antibodies, specifically including an anti-IL-31RA (neutralizing) antibody that recognizes domain 1 and/or domain 2 of human IL-31RA. As used herein, domain 1 of human IL-31RA designates the region from amino acid at position 53 to amino acid at position 152 (LPAKP to LENIA) in the amino acid sequence as set forth in SEQ ID NO: 11. Domain 2 designates the region from amino acid at position 153 to amino acid at position 259 (KTEPP to EEEAP) in the amino acid sequence as set forth in SEQ ID NO: 11.

Without any limitation, of the anti-IL-31RA neutralizing antibodies, more preferred is the anti-IL-31RA antibody described in WO 2010/064697 comprising an H chain (heavy chain) variable region comprising CDR1 as set forth in SEQ ID NO: 1, CDR2 as set forth in SEQ ID NO: 2, and CDR3 as set forth in SEQ ID NO: 3, and an L chain variable region comprising CDR1 as set forth in SEQ ID NO: 4, CDR2 as set forth in SEQ ID NO: 5, and CDR3 as set forth in SEQ ID NO: 6. Still more preferred is an anti-IL-31RA antibody comprising an H chain variable region as set forth in SEQ ID NO: 7 and an L chain (light chain) variable region as set forth in SEQ ID NO: 8. Particularly preferred is Nemolizumab (CIM331) which is an anti-IL-31RA antibody comprising an H chain as set forth in SEQ ID NO: 9 and an L chain as set forth in SEQ ID NO: 10.

Known methods for defining CDRs include the method according to Kabat et al. (Sequences of Proteins of Immunological Interest, 5th Ed (1991), Bethesda, Md.), the method according to Chothia et al. (Science (1986) 233, 755-758), and the method based on antigen-antibody contact regions (J Mol Biol (1996) 262, 732-745). Specifically, each of the methods defines CDRs as follows:

| CDR | Kabat | Chothia | Contact |
|-----|-------|---------|---------|
| L1 | L24-L34 | L24-L34 | L30-L36 |
| L2 | L50-L56 | L50-L56 | L46-L55 |
| L3 | L89-L97 | L89-L97 | L89-L96 |
| H1 | H31-H35B | H26-H32/34 | H30-H35B (Kabat numbering) |
| H1 | H31-H35 | H26-H32 | H30-H35 (Chothia numbering) |
| H2 | H50-H65 | H52-H56 | H47-H58 |
| H3 | H95-H102 | H95-H102 | H93-H101 |

An example of a preferred anti-IL-31RA neutralizing antibody of the present disclosure includes an anti-IL-31RA antibody comprising CDR1, CDR2, and CDR3 contained in the H chain variable region as set forth in SEQ ID NO: 7, and CDR1, CDR2, and CDR3 contained in the L chain variable region as set forth in SEQ ID NO: 8, as H chain CDR1, CDR2, and CDR3, and L chain CDR1, CDR2, and CDR3, respectively. The CDRs in such an antibody may be defined in accordance with any of the method according to Kabat et al., the method according to Chothia et al., and the method based on antigen-antibody contact regions, or in accordance with a combination of these methods.

Similarly, preferred as the anti-IL-31RA neutralizing antibody is an anti-IL-31RA antibody that binds to the same epitope as that of the anti-IL-31RA antibody defined by the above-described sequences of CDRs of the H chain and L chain, H chain and L chain variable region sequences, and full-length H chain and L chain sequences. An epitope refers to a specific structural unit of an antigen to which an antibody recognizes and binds. When the antigen is a polypeptide, the epitope typically consists of about 6 to 10 amino acids. Epitope identification can be performed using a method known to those skilled in the art, for example, a method of synthesizing peptides by fragmentation of the antigen, a method of introducing site-directed mutagenesis into the antigen (e.g., arginine/glutamic acid scanning, J Biol Chem (1995) 270, 21619-21625; J Biol Chem (2006) 281, 20464-20473), and a method of crystallizing an antigen-antibody complex (Using Antibodies: A Laboratory Manual (1999), Cold Spring Harbor Laboratory Press, New York). In the present disclosure, the recitation "binds to the same epitope" means that the epitopes to which two antibodies bind at least partially overlap each other. The degree of the overlap is, but not limited to, at least 10% or more, preferably 20% or more, 30% or more, 40% or more, 50% or more, 60% or more, 70% or more, and 80% or more, particularly preferably 90% or more, and most preferably 100%.

Similarly, preferred as the anti-IL-31RA neutralizing antibody is an anti-IL-31RA antibody that competes for binding to IL-31RA with the anti-IL-31RA antibody defined by the above-described sequences of CDRs of the H chain and L chain, H chain and L chain variable region sequences, and full-length H chain and L chain sequences. Whether the two antibodies compete with each other can be evaluated by using a competition binding assay utilizing ELISA, for example. A specific method is as follows: One of the two antibodies is pre-labeled with, for example, fluorescence. A system for detecting the binding of the antibody (labeled antibody) to the antigen is prepared. A comparison is made between the case where the other unlabeled antibody (test antibody) coexists and the case where the test antibody does not coexist in the system. If the level of binding of the labeled antibody to the antigen is decreased in the presence of the test antibody, it can be judged that the test antibody and the labeled antibody compete with each other. In the present disclosure, the degree of competition is, but not particularly limited to, at least 10% or more, preferably 20% or more, 30% or more, 40% or more, 50% or more, 60% or more, 70% or more, and 80% or more, and particularly preferably 90% or more, 95% or more, and 98% or more (that is, the level of binding of the other antibody is decreased).

Atopic dermatitis in the present disclosure may preferably be atopic dermatitis caused by IL-31 signaling or induced by IL-31, or atopic dermatitis showing responsiveness to the prevention and/or treatment with the IL-31 antagonist, but not limited thereto.

Pruritus in the present disclosure may be atopic dermatitis-induced pruritus, and may preferably be pruritus due to atopic dermatitis caused by IL-31 signaling or induced by IL-31, but not limited thereto. Moreover, pruritus may be pruritus due to atopic dermatitis which shows responsiveness to the prevention and/or treatment with the IL-31 antagonist.

Atopic dermatitis may be moderate to severe atopic dermatitis, for example, and may preferably be moderate or severe atopic dermatitis for which topical therapy is not sufficiently effective or is intolerable, or standard topical therapy is not sufficiently effective or is intolerable, or standard topical therapy is prohibited (for reasons such as contraindications). More preferably, atopic dermatitis may be moderate or severe atopic dermatitis for which topical therapy is not sufficiently effective or is intolerable.

For topical therapy, topical steroids (e.g., glucocorticoids or their derivatives such as prednisolone and hydrocortisone) and topical calcineurin inhibitors known as immunosuppressants (e.g., tacrolimus and pimecrolimus) are known, for example.

In addition to the topical steroids and topical calcineurin inhibitors, cyclosporin, methotrexate (MTX), or azathioprine (AZA), or antihistamines (various drugs are known as antihistaminic preparations, and are broadly classified into first-generation antihistamines and second-generation antihistamines) are known, for example, as therapeutic agents for atopic dermatitis.

More specifically, without any limitation, the following therapeutic methods are known for the treatment of atopic dermatitis ("Therapeutic Guidelines for Atopic Dermatitis", Fume et al., the Japanese journal of dermatology: 119 (8), pp. 1515-1534, 2009; "Guidelines of care for the management of atopic dermatitis: section 3. Management and treatment with phototherapy and systemic agents.", Sidbury R et al., J Am Acad Dermatol. (2014), pp. 327-337); and Saeki H, et al., J Dermatol 2009, 36, pp. 563-77).

(1) Cyclosporin Preparation (Brand Name: Neoral)
Typically, the cyclosporin preparation is orally administered to an adult at 3 mg/kg per day, calculated as cyclosporin, in two divided doses a day. The dose should not exceed 5 mg/kg per day, although it will vary as appropriate depending on the symptoms.

(2) Steroid Preparation for Oral Administration (Brand Name: Prednisolone Tablets)
Typically, the steroid preparation is orally administered to an adult at 5 mg to 60 mg per day, calculated as prednisolone (in the case of tablets, 1 to 12 tablets; in the case of powder, 0.5 g to 6 g), in one to four divided doses. The dose will vary as appropriate depending on the age or symptoms.

(3) Ultraviolet Therapy
It is generally said that a patient needs to visit the hospital once or twice a week, although there is no established manual or guidelines.

(4) Antihistamine Preparation (Brand Name: Allegra)
Typically, the antihistamine preparation is orally administered to an adult at a single dose of 60 mg, calculated as fexofenadine hydrochloride, twice a day. Typically, the antihistamine preparation is orally administered to a child 7 years or older and younger than 12 years at a single dose of 30 mg, calculated as fexofenadine hydrochloride, twice a day, and is orally administered to a child 12 years or older at a single dose of 60 mg, calculated as fexofenadine hydrochloride, twice a day. The dose will vary as appropriate depending on the symptoms.

(5) Topical Steroid Preparation (Brand Name: Fulmeta)
Typically, an appropriate amount of the topical steroid preparation is applied to an affected area once to several times a day. The amount will vary as appropriate depending on the symptoms.

(6) Topical Steroid Preparation (Brand Name: Locoid)
Typically, an appropriate amount of the topical steroid preparation is applied once to several times a day. The amount will vary as appropriate depending on the symptoms.

(7) Tacrolimus Preparation (Brand Name: Protopic)
Typically, an appropriate amount of the tacrolimus preparation is applied to an affected area once or twice a day for an adult. The applied amount should be up to 5 g per application.

(8) Pimecrolimus Preparation (Brand Name: Elidel)
Typically, an appropriate amount of the pimecrolimus preparation is applied twice a day. The amount will vary as appropriate depending on the symptoms.

The severity (e.g., mild, moderate, or severe) of atopic dermatitis may be classified based on a classification method known to those skilled in the art for scoring the degree of rash or itchiness felt by the subject, such as Shiratori's severity criteria, the below-described Visual Analogue Scale (VAS), Verbal Rating Scale (VRS) for pruritus, SCORing Atopic Dermatitis (SCORAD) established by the European Task Force on Atopic Dermatitis, Eczema Area and Severity Index (EASI) established in the United States, or static Investigator's Global Assessment (sIGA), for example.

The VAS, for example, consists of a 100-mm straight line, on which the subject (patient) indicates the intensity of itchiness at the time of the measurement by drawing a line between 0 to 100 mm, where 0 mm represents no itchiness, and 100 mm represents the worst imaginable itchiness. For example, a subject determined to have a VAS score of 40 mm or more may be recognized as having moderate to severe atopic dermatitis, and in one embodiment, the VAS score may be 45 mm or more, or 50 mm or more. Likewise, in the case of the VRS, for example, a subject classified into the level of "moderate itchiness" or higher may be recognized as having moderate to severe atopic dermatitis (Reich et al. 2012). Alternatively, for example, a subject determined to have an EASI score of 10 or more, a sIGA score of 3 or more, or a total score of 4 or more in the evaluation of the degree of itchiness in the daytime or nighttime based on Shiratori's severity criteria may be recognized as having moderate to severe atopic dermatitis. Alternatively, a subject in which rash with intense inflammation affects, for example, 5% or more of the body surface area may be recognized as having moderate to severe atopic dermatitis. Alternatively, a subject in which one or a combination of a plurality of indices of those mentioned herein are satisfied, as appropriate, may be recognized as having moderate to severe atopic dermatitis.

As used herein, the "subject" may preferably be an animal, and more preferably a mammal (a mouse, a rat, a rabbit, a dog, a monkey (e.g., a cynomolgus monkey), or the like), and particularly preferably a human, but not limited thereto. The human may be an adult (18 years or older) or a child (0 to younger than 18 years, for example, 6 months to younger than 18 years).

In one embodiment, the present disclosure relates to a lyophilized formulation and solution formulation for prevention and/or treatment of atopic dermatitis, comprising an IL-31 antagonist as an active ingredient.

In this case, the IL-31 antagonist may be intended to be repeatedly administered in equal amounts at the same dosing interval, using the predetermined dosing interval and the predetermined dose (dosage) that will be described in detail below.

In one embodiment, the lyophilized formulation and solution formulation of the present disclosure may be used for prevention and/or treatment of pruritus due to atopic dermatitis.

In a still further embodiment or another embodiment, the lyophilized formulation and solution formulation of the present disclosure may be used for improvement of sleep disturbance caused by atopic dermatitis, wherein the sleep disturbance may be caused by pruritus due to atopic dermatitis. The improvement of sleep disturbance may be characterized by, for example, an increase in the time from falling asleep to awakening, and/or a decrease in sleep onset latency (the time from going to bed to falling asleep).

In a still further embodiment or another embodiment, the lyophilized formulation and solution formulation of the present disclosure may be used for suppressing at least one symptom caused by atopic dermatitis selected from the group consisting of redness, induration, papules, edema, excoriations, and lichenification.

In one embodiment of the present disclosure, the prevention and/or treatment of atopic dermatitis may refer to, but not limited to, for example, administering a drug or the like to a subject who currently exhibits atopic dermatitis or various symptoms caused by atopic dermatitis (e.g., pruritus, redness, induration, papules, edema, excoriations, lichenification, decrease in QOL, and lack of sleep) to suppress one or more of these symptoms, and/or, for example, administering a drug or the like to a subject who has previously developed atopic dermatitis or various symptoms caused by atopic dermatitis to eliminate the development or reduce the incidence rate of one or more of these symptoms. The prevention and/or treatment of atopic dermatitis may be judged or determined to be useful for the prevention and/or treatment, as long as it improves any one of the various symptoms caused by atopic dermatitis, even though it cannot prevent and/or treat atopic dermatitis per se.

The subject potentially with atopic dermatitis may be a subject who has had atopic dermatitis in the past, and may have a risk of recurrence of the symptoms, or may be a subject with suspected atopic dermatitis before a doctor or the like makes a diagnosis or determination that the subject has atopic dermatitis, but not limited thereto.

In one embodiment, in some cases, the prevention and treatment of atopic dermatitis may be interpreted synonymously.

It is known that an IL-31 antagonist (CIM331) used in the present Examples demonstrated an improvement in sleep efficiency in the IL-31 antagonist-administered group in a single subcutaneous dose study of the IL-31 antagonist for patients with atopic dermatitis (WO 2016/167263).

Although atopic dermatitis is not necessarily a life-threatening serious disease, the symptoms associated with the disease significantly affect daily life. In particular, pruritus, which is the most characteristic symptom, is an unpleasant sensation that markedly lowers the patient's quality of life (QOL), and has been reported to hinder the patient's sleep (Zuberbier T, Orlow S J, Paller A S, Taieb A, Allen R, Hemanz-Hermosa J M, Ocampo-Candiani J, Cox M, Langeraar J, Simon J C. Patient perspective on the management of atopic dermatitis. J Allergy Clin Immunol 2006; 118: 226-32.). Furthermore, when the patient is a child, there is a significant burden not only on the affected child but also on the parents, and there is a report that the parents of a child with moderate or severe atopic dermatitis spend 3 hours every day in therapeutic treatment, and lose 1 to 2 hours of sleep every day (Su J C, Kemp A S, Varigos G A, Nolan T M. Atopic eczema: its impact on the family and financial cost. Arch Dis Chil 1997; 76: 159-62.).

In another embodiment, therefore, the present disclosure relates to a lyophilized formulation and solution formulation for prevention and/or treatment of atopic dermatitis comprising an IL-31 antagonist as an active ingredient, which is further for improvement of sleep disturbance caused by atopic dermatitis. Alternatively, in a further embodiment or another embodiment, the present disclosure relates to a lyophilized formulation and solution formulation for improvement of a decrease in QOL caused by atopic dermatitis. The improvement of sleep disturbance may be characterized by, for example, an increase in the time from falling asleep to awakening, and/or a decrease in sleep onset latency (the time from going to bed to falling asleep).

As used herein, the recitation "repeatedly administered in equal amounts at the same dosing interval" intends to mean that the dose at which the IL-31 antagonist of the present disclosure is initially administered to a subject (initial dose) is equal to a continuous dose at which the IL-31 antagonist is subsequently administered (namely, the dose to be continuously administered subsequent to the administration of the initial dose), and the IL-31 antagonist is administered at an equal dosing interval (interval between doses). Specifically, for example, the above-described recitation means that the interval between the administration of the initial dose and the administration of the first continuous dose, or every interval between the administration of the n-th (n is an integer of 1 or more) continuous dose and the administration of the (n+1)-th continuous dose is equal, and the doses are equal. Those skilled in the art will naturally understand that, for decided dosing intervals (e.g., every 4 weeks in the case where the dosing interval is decided to be every 4 weeks), each dosing interval has a "tolerable range", and those skilled in the art can decide the tolerable range, as appropriate.

In the present invention, the term "stable antibody-containing formulation" refers to a formulation in which aggregates and/or components with charge heterogeneity from proteins such as antibodies are difficult to be generated, i.e., the formulations in which deterioration reactions, including generation of insoluble aggregates, soluble aggregates, components with charge heterogeneity, are difficult to occur in the formulation.

"Components with charge heterogeneity" refer to components having protein surface charges that are different from those of the major component due to deamidation, oxidation, hydrolysis, and such.

Amounts of aggregates can be measured by size exclusion chromatography (SEC), SDS polyacrylamide gel electrophoresis (SDS-PAGE), capillary SDS gel electrophoresis (CE-SDS), dynamic light scattering (DLS), light obscuration automated microparticle counter (HIAC), flow imaging, Analytical Ultracentrifuge (AUC) and such, and measurements by size exclusion chromatography (SEC) are preferred in the present invention. It is thought that as measurement conditions, samples are measured using a column (TOSOH, TSKgel G3000SWXL), using 50 mmol/L phosphate buffer (pH 7.0), 300 mmol/L sodium chloride, 0.05% sodium azide as a mobile phase at a flow rate of 0.5 mL/min, but conditions are not limited thereto. In one embodiment, amounts of aggregates are measured by the methods described in Examples herein.

Components with charge heterogeneity can be measured by ion exchange chromatography (IEC), specifically cation exchange chromatography or anion exchange chromatography, isoelectric focusing and such, and in the present invention, the measurements are preferably measurements by anion exchange chromatography. Amounts of components with charge heterogeneity in samples can be measured by ion exchange chromatography (IEC) using a column (TOSOH, TSKgel DEAE-NPR), using 25 mmol/L Tris-HCl buffer (pH 7.5) as mobile phase A and 25 mmol/L Tris-HCl buffer (pH 7.5), 250 mmol/L sodium chloride as mobile phase B at a flow rate of 1.0 mL/min, but methods are not limited thereto. In one embodiment, components with charge heterogeneity are measured by the methods described in Examples herein.

In the present invention, "polypeptide" generally refers to peptides and proteins having a length of approximately ten amino acids or longer. Ordinarily, they are biologically derived polypeptides, but are not particularly limited thereto, and may be, for example, polypeptides comprising an artificially designed sequence. Furthermore, they may be any naturally-occurring polypeptides, synthetic polypeptides, recombinant polypeptides, or such. Additionally, fragments of the above-mentioned polypeptides are also included in the polypeptides of the present invention.

The term "antibody" is used in the broadest sense, and includes monoclonal antibodies, polyclonal antibodies, dimers, multimers, multispecific antibodies (such as bispecific antibodies), antibody derivatives, and modified antibodies (Miller K et al. J Immunol. 2003, 170(9), 4854-61) so long as they show a desired biological activity. The antibodies may be mouse antibodies, human antibodies, humanized antibodies, chimeric antibodies, or those derived from another species, or artificially synthesized antibodies. The antibodies disclosed herein can be of any type (for example, IgG IgE, IgM, IgD, and IgA), class (for example, IgG1, IgG2, IgG3, IgG4, IgA1 and IgA2) or subclass of immunoglobulin molecules. The immunoglobulins can be derived from any species (for example, human, mouse, or rabbit). The terms "antibody", "immune globulin" and "immunoglobulin" are used interchangeably in a broad sense.

Recombinant antibodies produced by using genetic engineering techniques can be used as the antibodies. A recombinant antibody can be obtained by cloning a DNA encoding the antibody from hybridomas or antibody-producing cells such as sensitized lymphocytes that produce antibodies; inserting this into a vector; and then introducing it into hosts (host cells) to produce the antibody.

Antibodies of the present invention can be produced by methods known to those skilled in the art. Specifically, a DNA encoding the antibody of interest is inserted into an expression vector. The insertion into the expression vector is carried out such that the expression will take place under the control of expression regulatory regions such as an enhancer and a promoter. Next, host cells are transformed using this expression vector to express the antibody. Appropriate combinations of a host and an expression vector can be used in this case.

The antibodies of the present invention thus obtained can be isolated from the inside of host cells or the outside of the cells (medium, etc.), and purified to be substantially pure, homogeneous antibodies. The antibodies can be separated and purified by methods ordinarily used for separating and purifying antibodies, and the methods are not limited in any way. For example, the antibodies can be separated and purified by appropriately selecting and combining column chromatography, filtration, ultrafiltration, salting-out, solvent precipitation, solvent extraction, distillation, immunoprecipitation, SDS-polyacrylamide gel electrophoresis, isoelectrofocusing, dialysis, recrystallization, and such.

The present inventors examined the effects of various additives to evaluate stability of samples containing the above-mentioned anti-IL-31RA antibody (CIM331) during storage by thermal acceleration test. As a result, the present inventors found that by preparing lyophilized formulations from solutions added with arginine-hydrochloride and sucrose or trehalose, aggregate formation was suppressed compared to when they do not comprise stabilizers or bulking agents (fillers), when sodium chloride is added as a stabilizer, or when other sugars are added as a bulking agent. The present inventors also found that subvisible particles formation and aggregate formation are suppressed by adding Poloxamer 188 and/or Polysorbate 20, which are nonionic surfactants, to an antibody-containing solution. Furthermore, the present inventors found that aggregate formation and components with charge heterogeneity are suppressed at pH 6 to pH 8 in antibody-containing solutions comprising arginine-hydrochloride, sucrose or trehalose, and nonionic surfactant.

The concentration (amount) of arginine in formulations of the present invention is preferably 45 mM to 150 mM. Examples of the arginine concentration (amount) include 45 mM, 75 mM, 92 mM, 102 mM and 150 mM.

The solution pH of a formulation of the present invention is preferably 6 to 8, more preferably 6.5 to 7.5, and even more preferably 7.

The formulations of the present invention can comprise as a buffer, for example, Tris buffer. Tris buffer includes, for example, tris(hydroxymethyl)aminomethane and/or salts thereof, e.g., tris(hydroxymethyl)aminomethane-hydrochloride, tris(hydroxymethyl)aminomethane-aspartate, tris(hydroxymethyl)aminomethane-glutamate or tris(hydroxymethyl)aminomethane-acetate. Amount of Tris buffer added to the formulation of the present invention is preferably 6 mM to 20 mM, and for example, 6 mM, 10 mM, 12.3 mM, 13.6 mM, or 20 mM.

Surfactants contained in formulations of the present invention are, for example Polysorbate 20 (PS20), and Pluronic F-68 (Poloxamer 188: polyoxyethylene (160) polyoxypropylene (30) glycol), and Poloxamer 188 is particularly preferred. The amount of Poloxamer 188 (or PX188)

added to a formulation of the present invention is preferably 0.15 mg/mL to 0.5 mg/mL. Examples of the amount of Poloxamer 188 added to the formulation include 0.15 mg/mL, 0.25 mg/mL, 0.31 mg/mL, 0.34 mg/mL, and 0.50 mg/mL.

The formulations of the present invention may further contain sugars. Preferred sugars used in the present invention are sucrose, trehalose, mannitol, and lactose, and sucrose and trehalose are particularly preferred.

The amount of sugars added to the formulations of the present invention is generally 1 mM to 1000 mM, preferably 5 mM to 500 mM, and more preferably 10 mM to 300 mM, for example 75 mM to 250 mM, and for example 75 mM, 125 mM, 154 mM, 170 mM, or 250 mM.

If needed, the formulations of the present invention may additionally contain appropriate cryoprotectants, suspending agents, solubilizing agents, tonicity agents, preservatives, adsorption inhibitors, diluents, excipients, pH adjustors, analgesics, sulfur-containing reducing agents, antioxidants, and such.

Cryoprotectants include, for example, sugars such as trehalose, sucrose, and sorbitol.

Solubilizing agents include, for example, polyoxyethylene hardened castor oil, Polysorbate 80, nicotinamide, polyoxyethylene sorbitan monolaurate, macrogol, and castor oil fatty acid ethyl ester.

Tonicity agents include, for example, sodium chloride, potassium chloride, and calcium chloride.

Preservatives include, for example, methyl-p-hydroxybenzoate, ethyl-p-hydroxybenzoate, sorbic acid, phenol, cresol, and chlorocresol.

Adsorption inhibitors include, for example, human serum albumin, lecithin, dextran, ethylene oxide/propylene oxide copolymer, hydroxypropyl cellulose, methyl cellulose, polyoxyethylene hardened castor oil, and polyethylene glycol.

Sulfur-containing reducing agents include, for example, those containing sulfhydryl groups such as N-acetylcysteine, N-acetylhomocysteine, thioctic acid, thiodiglycol, thioethanol amine, thioglycerol, thiosorbitol, thioglycolic acid and salts thereof, sodium thiosulfate, glutathione, and thioalkanoic acids having one to seven carbon atoms.

Antioxidants include, for example, erythorbic acid, dibutylhydroxytoluene, butylhydroxyanisole, α-tocopherol, tocopherol acetate, L-ascorbic acid and salts thereof, L-ascorbic acid palmitate, L-ascorbic acid stearate, sodium hydrogen sulfite, sodium sulfite, triamyl gallate, propyl gallate, and chelating agents such as disodium ethylenediamine tetraacetate (EDTA), sodium pyrophosphate, and sodium metaphosphate.

The antibody-containing formulations of the present invention can be administered to a patient via any appropriate route, for example, by bolus injection or continuous infusion for a certain period, intravenously, intramuscularly, or subcutaneously. Intravenous administration or subcutaneous administration is preferred.

Dose of Nemolizumab (CIM331) is, for example, 0.001 mg/kg to 1000 mg/kg, and dosing interval is at least one day or longer.

More specifically, for example, Nemolizumab (CIM331) is administered repeatedly to a subject affected with atopic dermatitis or at a risk of being affected with atopic dermatitis at 0.1 mg to 1000 mg/body/2 weeks, 0.1 mg to 1000 mg/body/4 weeks, or 0.1 mg to 1000 mg/body/8 weeks, or 0.01 mg to 10 mg/kg/2 weeks, 0.01 mg to 10 mg/kg/4 weeks, or 0.01 mg to 10 mg/kg/8 weeks, preferably 0.5 mg/kg/4 weeks, or 50 mg to 75 mg/body/4 weeks in equal amounts and at the same dosing interval. Alternatively, Nemolizumab (CIM331) is repeatedly administered at 60 mg/body/4 weeks at the same dose and at the same dosing interval. Alternatively, Nemolizumab (CIM331) is administered at a dosing interval of four weeks, and repeatedly administered at 60 mg/body as an initial dose and at 30 mg/body as a continuous dose. Those skilled in the art will naturally understand that when a lyophilized formulation comprising one dose Nemolizumab (CIM331) is enclosed in a container (vial, cartridge or syringe), considering the loss of reconstituted drug solution when administered, an excess amount of lyophilized formulation would be filled to ensure, from one container (vial, cartridge or syringe), the amount sufficient to administer one dose Nemolizumab (CIM331).

Another embodiment of the present invention is a method for stabilizing an antibody in an antibody-containing formulation. For example, the embodiment is a method for stabilizing an antibody in an antibody-containing solution formulation, the method comprising adding arginine and/or salts thereof, and sucrose and/or trehalose to the solution. In addition, for example the embodiment is a method for stabilizing an antibody in an antibody-containing lyophilized formulation, the method comprising preparing an antibody-containing lyophilized formulation by freeze-drying an antibody-containing solution comprising arginine and/or salts thereof, and sucrose and/or trehalose.

In addition, another embodiment of the present invention is a method for suppressing antibody aggregation (aggregate formation) in an antibody-containing formulation. For example, the embodiment is a method for suppressing antibody aggregation (aggregate formation) in an antibody-containing solution formulation, the method comprising adding arginine and/or salts thereof, and sucrose and/or trehalose to the solution. Furthermore, for example, the embodiment is a method for suppressing antibody aggregation (aggregate formation) in an antibody-containing lyophilized formulation, the method comprising preparing an antibody-containing lyophilized formulation by freeze-drying an antibody-containing solution comprising arginine and/or salts thereof, and sucrose and/or trehalose.

Another embodiment of the present invention is a method for reducing components with charge heterogeneity in an antibody-containing formulation. For example, the embodiment is a method for reducing components with charge heterogeneity in an antibody-containing solution formulation, the method comprising adding arginine and/or salts thereof, and sucrose and/or trehalose to the solution. Furthermore, for example, the embodiment is a method for reducing components with charge heterogeneity in an antibody-containing lyophilized formulation, the method comprising preparing an antibody-containing lyophilized formulation by freeze-drying an antibody-containing solution comprising arginine and/or salts thereof, and sucrose and/or trehalose.

Furthermore, in the above-mentioned methods for stabilizing an antibody, methods for suppressing antibody aggregation (aggregates formation), and methods for reducing components with charge heterogeneity, concentration of arginine-hydrochloride (Arg-HCl) in the solution is preferably 45 mmol/L to 150 mmol/L, concentration of sucrose or trehalose in a solution is preferably 75 mmol/L to 250 mmol/L.

In the above-mentioned methods for stabilizing an antibody, methods for suppressing antibody aggregation (aggregate formation), and methods for reducing components with charge heterogeneity, the antibody is preferably Nemolizumab (CIM331).

As used herein, aspects referred to by the expression "comprising" include those referred to by the expression "essentially consisting of", and those referred to by the expression "consisting of".

Numerical values recited herein may vary within a certain range, for example, depending on the instruments or equipment, measurement conditions, and procedure used by those skilled in the art, and so long as they are within a range that allows the objective of the invention to be accomplished, they may encompass a deviation of approximately 10%, for example.

All patents and references explicitly cited herein are incorporated by reference into this specification in its entirety.

The present invention will be further illustrated by the Examples below, but it is not to be construed as being limited thereto.

EXAMPLE

Definition

Experimental Methods

To adjust pH, formulations prepared in each Example contain 6 mmol/L to 20 mmol/L Tris-HCl, which do not contribute to the stability of CIM331 (an anti-IL-31RA antibody comprising the H chain of SEQ ID NO: 9 and the L chain of SEQ ID NO: 10).

Thermal acceleration study of solution formulations was performed at 40° C./75% RH. Meanwhile, as lyophilized formulations are generally more stable, thermal acceleration study of lyophilized formulations was performed at a higher temperature, 50° C./75% RH.

In Example 3, to verify effects of nonionic surfactants, shaking study was performed.

Analysis Methods

Regarding measurements of amounts of CIM331 aggregate, considering the accuracy of analysis methods, it can be judged that there is significant difference when the percentage of aggregates has 0.07% or higher difference.

Regarding measurements of components with charge heterogeneity of CIM331, considering the accuracy of analysis methods, it can be judged that there is significant difference when the difference is 1.3% or higher for Basic region, 1.4% or higher for Main region, and 0.6% or higher for Acidic region.

Since stability is different between solution formulation and lyophilized formulation, results from analysis methods cannot similarly be interpreted between solution formulation and lyophilized formulation.

Example 1

Aggregate Suppressing Effects of Arginine on the Humanized IgG2 Antibody CIM331 during Thermal Accelerated Storage

[1-1] Stability assessment of lyophilized formulations (1) Materials

CIM331 is a monoclonal antibody that binds to IL-31RA, and is a humanized IgG2 antibody expected to lead to the treatment of atopic dermatitis and such, by inhibiting the function of IL-31, which is identified as a pruritus-inducible cytokine.

(2) Test Samples

Various prepared solutions comprising 30 mg/mL CIM331, 6 mmol/L Tris-HCl, 75 mmol/L Sucrose, 0.15 mg/mL Poloxamer 188, and either one of 45 mmol/L Arg-HCl or 45 mmol/L NaCl as a stabilizer, and a prepared solution not comprising a stabilizer were prepared and filled into glass vials (2 mL/vial). Filled drug solutions were lyophilized under the condition shown below.

| Temperature | Time | Pressure |
|---|---|---|
| Room temperature → −45° C. | 1 hour | — |
| −45° C. | 6 hours | — |
| −45° C. → 0° C. | 50 minutes | 10 Pa |
| 0° C. | 50 hours | 10 Pa |
| 0° C. → 30° C. | 30 minutes | 6 Pa |
| 30° C. | 10 hours | 6 Pa |

After humanized antibody-containing lyophilized formulations prepared as such were left to stand in a 50° C./75% RH incubator for 8 weeks, reconstituted solutions prepared such that the CIM331 concentration became 100 mg/mL by adding ultra-pure water were used as test samples.

(3) Method for Measuring Amounts of CIM331 Aggregates and Method for Calculating Amounts of CIM331 Aggregates Samples were measured for their amounts of aggregates by size exclusion chromatography (SEC) at a flow rate of 0.5 mL/min using a column (TOSOH, TSKgel G3000SWXL), and 50 mmol/L phosphate buffer (pH 7.0), 300 mmol/L sodium chloride, 0.05% sodium azide as a mobile phase.

Among detected peaks, a peak showing the maximum area and height is defined as monomer body, and peaks detected before the monomer body were collectively defined as aggregates (HMWS).

For all peaks, area was calculated and peak area ratio of target peak was determined according to the equation below.

$$\text{Peak area ratio of target peak (\%)} = \frac{\text{Peak area of target peak}}{\text{Peak area of target peak} + \text{sum of other peak areas}} \times 100$$

(4) Results

The obtained results are shown in Table 1.

TABLE 1

| Stabilizer | | Arg-HCl | Without stabilizer | NaCl |
|---|---|---|---|---|
| HMWS [%] | Initial | 0.52 | 0.61 | 0.59 |
| | 50° C. after 8 weeks | 1.30 | 3.79 | 2.10 |
| Relative increase rate [%]* | | 24.5 | 100.0 | 47.5 |

*From HMWS increased amount when a stabilizer was not added and HMWS increased amount when each stabilizer was added, relative increase rates compared to when a stabilizer was not added were calculated.

As is apparent from Table 1, a sample added with arginine-hydrochloride showed high aggregate-suppressing effect compared to a sample not added with a stabilizer and a sample added with sodium chloride eight weeks after 50° C./75% RH thermal acceleration.

[1-2] Stability Assessment of Solution Formulations (1) Materials

The antibody described in [1-1] was used.

(2) Test Samples

Various prepared solutions comprising 100 mg/mL CIM331, 20 mmol/L Tris-HCl, 250 mmol/L Sucrose, 0.5 mg/mL Poloxamer 188, pH 7, and either one of 150 mmol/L Arg-HCl or 150 mmol/L NaCl as a stabilizer, and a prepared solution not comprising a stabilizer were prepared and filled into glass vials (1 mL/vial). After humanized antibody-containing solution formulations prepared as such were left to stand in a 40° C./75% RH incubator for four weeks, they were used as test samples.

(3) Method for Measuring Amounts of CIM331 aggregates and Method for Calculating Amounts of CIM331 Aggregates The methods were performed according to the methods described in [1-1].

(4) Results

The obtained results are shown in Table 2.

TABLE 2

| Stabilizer | | Arg-HCl | Without stabilizer | NaCl |
|---|---|---|---|---|
| HMWS [%] | Initial | 0.55 | 0.63 | 0.65 |
| | 40° C. after 4 weeks | 1.00 | 1.69 | 1.48 |
| Relative increase rate [%]* | | 42.5 | 100.0 | 78.3 |

*From HMWS increased amount when a stabilizer was not added and HMWS increased amount when each stabilizer was added, relative increase rates compared to when a stabilizer was not added were calculated.

As is apparent from Table 2, samples added with arginine hydrochloride showed high aggregate-suppressing effect compared to a sample not added with a stabilizer and a sample added with sodium chloride four weeks after 40° C./75% RH thermal acceleration.

Example 2

Aggregate-Suppressing Effects of Sucrose and Trehalose on the Humanized IgG2 Antibody CIM331 During Thermal Accelerated Storage (1) Materials The antibody described in Example 1 was used.

(2) Test Samples

Various prepared solutions comprising 30 mg/mL CIM331, 6 mmol/L Tris-HCl, 45 mmol/L Arg-HCl, 0.15 mg/mL Poloxamer 188, and any one of 75 mmol/L Sucrose, 75 mmol/L Mannitol, 75 mmol/L Glucose, 75 mmol/L Lactose or 75 mmol/L Trehalose as a bulking agent, and a prepared solution not comprising a bulking agent were prepared and filled into glass vials (2 mL/vial). Filled drug solutions were lyophilized under the condition shown below.

| Temperature | Time | Pressure |
|---|---|---|
| Room temperature → −45° C. | 1 hour | — |
| −45° C. | 6 hours | — |
| −45° C. → 0° C. | 50 minutes | 10 Pa |
| 0° C. | 50 hours | 10 Pa |
| 0° C. → 30° C. | 30 minutes | 6 Pa |
| 30° C. | 10 hours | 6 Pa |

After humanized antibody-containing lyophilized formulations prepared as such were left to stand in a 50° C./75% RH incubator for eight weeks, reconstituted solutions prepared by adding ultra-pure water such that the CIM331 concentration became 100 mg/mL were used as test samples.

(3) Method for Measuring Amounts of CIM331 Aggregates and Method for Calculating Amounts of CIM331 Aggregates The methods were performed according to the methods described in Example 1.

(4) Results

The obtained results are shown in Table 3.

TABLE 3

| Bulking agent | | Sucrose | Without bulking agent | Mannitol | Glucose | Lactose | Trehalose |
|---|---|---|---|---|---|---|---|
| HMWS [%] | Initial | 0.52 | 0.71 | 0.50 | 0.53 | 0.54 | 0.50 |
| | 50° C. after 8 weeks | 1.30 | 8.51 | 2.87 | 13.25 | 4.27 | 1.96 |
| Relative increase rate [%]* | | 10.0 | 100.0 | 30.4 | 163.1 | 47.8 | 18.7 |

*From HMWS increased amount when a bulking agent was not added and HMWS increased amount when each bulking agent was added, relative increase rates compared to when a bulking agent was not added were calculated.

As is apparent from Table 3, samples added with sucrose or trehalose both showed relative increase rate of the 10% range, and showed high aggregate-suppressing effect compared to a sample not added with a bulking agent and samples added with other bulking agents eight weeks after 50° C./75% RH thermal acceleration.

Example 3

Subvisible Particles Formation-Suppressing Effects and Solution State-Stabilizing Effects of Nonionic Surfactants on the Humanized IgG2 Antibody CIM331 During Shaking Stress Test (1) Materials The antibody described in Example 1 was used.

(2) Test Samples

Various prepared solutions comprising 100 mg/mL CIM331, 20 mmol/L Tris-HCl, pH 7, 150 mmol/L Arg-HCl, 250 mmol/L Sucrose, and either one of 0.5 mg/mL Poloxamer 188 or 0.5 mg/mL Polysorbate 20 as a nonionic surfactant, and a prepared solution not comprising a nonionic surfactant were prepared and filled into glass vials (1 mL/vial). After humanized antibody-containing solution formulations prepared as such were shaken at room temperature for three days at a speed of approximately 200 rpm, they were used as test samples.

(3) Method for Measuring Subvisible Particles

Number of subvisible particles were counted using a liquid particle counter (Hach Ultra Analytics, Model 9703).

(4) Method for Measuring Amounts of CIM331 Aggregates and Method for Calculating Amounts of CIM331 Aggregates The methods were performed according to the methods described in Example 1.

(5) Results

The obtained results are shown in Tables 4 and 5.

TABLE 4

| Surfactant | | Poloxamer 188 | Without nonionic surfactant | Polysorbate 20 |
|---|---|---|---|---|
| Subvisible particles counts (≥10 μm) | Initial | 3 | 3 | 21 |
| | 200 rpm after 3 days | 3 | 404200 | 11 |
| Subvisible particles counts (≥25 μm) | Initial | 1 | 1 | 7 |
| | 200 rpm after 3 days | 1 | 26640 | 3 |

TABLE 5

| Surfactant | | Poloxamer 188 | Without nonionic surfactant | Polysorbate 20 |
|---|---|---|---|---|
| HMWS [%] | Initial | 0.55 | 0.53 | 0.51 |
| | 200 rpm after 3 days | 0.61 | 1.17 | 0.56 |
| Relative increase rate [%]* | | 9.4 | 100.0 | 7.8 |

*From HMWS increased amount when a nonionic surfactant was not added and HMWS increased amount when each nonionic surfactant was added, relative increase rates compared to when a nonionic surfactant was not added were calculated.

As is apparent from Tables 4 and 5, samples containing Poloxamer 188 or Polysorbate 20, which is a nonionic surfactant, showed high subvisible particles formation-suppressing effect and high aggregate-suppressing effect in samples after shaking at room temperature for three days at a speed of approximately 200 rpm.

Example 4

Effects of pH on Stability of the Humanized IgG2 Antibody CIM331 During Thermal Accelerated Storage (1) Materials The antibody described in Example 1 was used.

(2) Test Samples

Various prepared solutions comprising 100 mg/mL CIM331, 20 mmol/L Tris-HCl, 150 mmol/L Arg-HCl, 250 mmol/L Sucrose, and 0.5 mg/mL Poloxamer 188, of which pH is any one of pH 6, pH 7 or pH 8, were prepared and filled into glass vials (1 mL/vial). After humanized antibody-containing solution formulations prepared as such were left to stand in a 40° C./75% RH incubator for four weeks, they were used as test samples.

(3) Method for Measuring Amounts of CIM331 Aggregates and Method for Calculating Amounts of CIM331 Aggregates The methods were performed according to the methods described in Example 1.

(4) Methods for Measuring and Calculating Components with Charge Heterogeneity of CIM331

Samples were measured for their amounts of components with charge heterogeneity by ion-exchange chromatography (IEC) at a flow rate of 1.0 mL/min using column (TOSOH, TSKgel DEAE-NPR), and 25 mmol/L Tris-HCl buffer (pH 7.5) as mobile phase A and 25 mmol/L Tris-HCl buffer (pH 7.5), 250 mmol/L sodium chloride as mobile phase B.

Among detected peaks, a peak showing maximum area and height was defined as Main region, peaks detected before Main region were collectively defined as Basic region, peaks detected after Main region were collectively defined as Acidic region.

For all peaks, area was calculated, and peak area ratio of target peak was determined according to the equation below.

$$\text{Peak area ratio of target peak } (\%) = \frac{\text{Peak area of target peak}}{\text{Peak area of target peak} + \text{sum of other peak areas}} \times 100$$

(5) Results

The obtained results are shown in Table 6.

TABLE 6

| pH | | pH6 | pH7 | pH8 |
|---|---|---|---|---|
| HMWS [%] | Initial | 0.51 | 0.55 | 0.56 |
| | 40° C. after 4 weeks | 1.16 | 1.00 | 2.07 |
| Main region [%] | Initial | 79.9 | 79.8 | 79.7 |
| | 40° C. after 4 weeks | 32.9 | 49.8 | 43.1 |

As is apparent from Table 6, samples of pH 6 to pH 8 showed sufficient stability four weeks after 40° C./75% RH thermal acceleration, and in particular in a sample at pH 7, high aggregate-suppressing effects and effects of suppressing components with charge heterogeneity were achieved.

Example 5

Effects of Humanized IgG2 Antibody CIM331 Concentration and Concentrations of Other Formulation Components on Stability During Thermal Accelerated Storage (1) Materials The antibody described in Example 1 was used.

(2) Test Samples

Various prepared solutions comprising 100 mg/mL or 50 mg/mL CIM331, 20 mmol/L or 10 mmol/L Tris-HCl, 150 mmol/L or 75 mmol/L Arg-HCl as a stabilizer, 250 mmol/L or 125 mmol/L Sucrose as a bulking agent, and 0.5 mg/mL or 0.25 mg/mL Poloxamer 188 as a nonionic surfactant, and prepared solutions comprising 6 mmol/L Tris-HCl, 45 mmol/L Arg-HCl, 75 mmol/L Sucrose, 0.15 mg/mL Poloxamer 188, and 30 mg/mL, 15 mg/mL or 6 mg/mL CIM331 were prepared and filled into glass vials (2 mL/vial). Filled drug solutions were lyophilized under the condition shown below.

| Temperature | Time | Pressure |
|---|---|---|
| Room temperature → −45° C. | 1 hour | — |
| −45° C. | 6 hours | — |
| −45° C. → 0° C. | 50 minutes | 10 Pa |
| 0° C. | 50 hours | 10 Pa |
| 0° C. → 30° C. | 30 minutes | 6 Pa |
| 30° C. | 10 hours | 6 Pa |

After humanized antibody-containing lyophilized formulations prepared as such were left to stand in a 50° C./75% RH incubator for eight weeks, reconstituted solutions prepared by adding ultra-pure water such that CIM331 concentrations became as shown below were used as test samples.

| CIM331 Concentration [mg/mL] | | | | | |
|---|---|---|---|---|---|
| Solution before lyophilization | 100 | 50 | 30 | 15 | 6 |
| Reconstituted solution | 100 | 50 | 100 | 50 | 20 |

(3) Method for Measuring Amounts of CIM331 Aggregates and Method for Calculating Amounts of CIM331 Aggregates The methods were performed according to the methods described in Example 1.

(4) Methods for Measuring and Calculating Components with Charge Heterogeneity of CIM331

The methods were performed according to the methods described in Example 4.

(5) Results

The obtained results are shown in Table 7.

TABLE 7

| CIM331 Concentration [mg/mL] (Before lyophilization) | | 100 | 50 | 30 | 15 | 6 |
|---|---|---|---|---|---|---|
| Formulation components | | 20 mmol/L Tris-HCl, 150 mmol/L Arg-HCl, 250 mmol/L Sucrose, 0.5 mg/mL Poloxamer 188 | 10 mmol/L Tris-HCl, 75 mmol/L Arg-HCl, 125 mmol/L Sucrose, 0.25 mg/mL Poloxamer 188 | | 6 mmol/L Tris-HCl, 45 mmol/L Arg-HCl, 75 mmol/L Sucrose, 0.15 mg/mL Poloxamer 188 | |
| HMWS [%] | Initial | 0.52 | 0.49 | 0.52 | 0.47 | 0.44 |
| | 50° C. after 8 weeks | 1.31 | 1.29 | 1.30 | 0.62 | 0.47 |
| Basic region [%] | Initial | 14.8 | 14.2 | 13.9 | 14.2 | 14.3 |
| | 50° C. after 8 weeks | 16.5 | 16.6 | 17.0 | 17.0 | 17.3 |

As is apparent from Table 7, samples comprising tested concentrations of each of the components, i.e., samples comprising 6 mg/mL to 100 mg/mL CIM331, 6 mmol/L to 20 mmol/L Tris-HCl, 45 mmol/L to 150 mmol/L Arg-HCl, 75 mmol/L to 250 mmol/L Sucrose, and 0.15 mg/mL to 0.5 mg/mL Poloxamer 188 had sufficient stability eight weeks after 50° C./75% RH thermal acceleration. Regarding HMWS, when formulation components other than antibody were the same concentrations, samples comprising lower-concentrated antibody showed more excellent stability.

Example 6

Effects of Arginine in Suppressing Aggregates and Components with Charge Heterogeneity of Humanized IgG2 Antibody CIM331 during Thermal Accelerated Storage

[6-1] Stability Assessment of Lyophilized Formulations (1) Materials

The antibody described in Example 1 was used.

(2) Test Samples

Various prepared solutions containing 30 mg/mL CIM331, 6 mmol/L Tris-HCl, pH7, 75 mmol/L sucrose, 0.15 mg/mL Poloxamer 188, and any of 45 mmol/L Arg-HCl, 45 mmol/L histidine, 45 mmol/L lysine-HCl, and 45 mmol/L glycine as a stabilizer, were prepared and filled into glass vials (2 mL/vial). Filled drug solutions were lyophilized under the conditions shown below.

| Temperature | Time | Pressure |
|---|---|---|
| Room temperature → −45° C. | 1 hour | — |
| −45° C. | 6 hours | — |
| −45° C. → 0° C. | 50 minutes | 10 Pa |
| 0° C. | 50 hours | 10 Pa |
| 0° C. → 30° C. | 30 minutes | 6 Pa |
| 5° C. | 10 hours | 6 Pa |

After humanized antibody-containing lyophilized formulations prepared as such were left to stand in a 50° C./75% RH incubator for eight weeks, reconstituted solutions prepared such that the CIM331 concentration became 100 mg/mL by adding ultra-pure water were used as test samples.

(3) Method for Measuring Amounts of CIM331 Aggregates and Method for Calculating Amounts of CIM331 Aggregates The methods were performed according to the methods described in Example 1.

(4) Methods for Measuring and Calculating Components with Charge Heterogeneity of CIM331

The methods were performed according to the methods described in Example 4.

(5) Results

The obtained results are shown in Table 8.

TABLE 8

| Stabilizer | | Arg-HCl | Histidine | Lysine-HCl | Glycine |
|---|---|---|---|---|---|
| HMWS [%] | Initial | 0.49 | 0.45 | 0.51 | 0.56 |
| | 50° C. after 8 weeks | 1.29 | 1.82 | 1.65 | 2.45 |
| | HMWS increase [%] | 0.80 | 1.37 | 1.14 | 1.89 |
| Main region [%] | Initial | 78.8 | 78.3 | 78.4 | 78.4 |
| | 50° C. after 8 weeks | 74.8 | 71.4 | 71.2 | 68.2 |
| | Main region decrease [%] | 4.0 | 6.9 | 7.2 | 10.2 |

As is apparent from Table 8, a sample added with arginine-hydrochloride showed the highest aggregate-suppressing effect and effect of suppressing components with charge heterogeneity as compared to samples added with histidine, lysine-hydrochloride, or glycine eight weeks after 50° C./75% RH thermal acceleration.

[6-2] Stability Assessment of Solution Formulations
(1) Materials
The antibody described in Example 1 was used.
(2) Test Samples
Various prepared solutions comprising 100 mg/mL CIM331, 20 mmol/L Tris-HCl, pH7, 250 mmol/L Sucrose, 0.50 mg/mL Poloxamer 188, and any of 150 mmol/L Arg-HCl, 150 mmol/L histidine, 150 mmol/L lysine-HCl, and 150 mmol/L glycine as a stabilizer were prepared and filled into glass vials (1 mL/vial). After humanized antibody-containing solution formulations prepared as such were left to stand in a 40° C./75% RH incubator for four weeks, they were used as test samples.
(3) Methods for Measuring and Calculating Components with Charge Heterogeneity of CIM331
The methods were performed according to the methods described in Example 4.
(4) Results
The obtained results are shown in Table 9.

TABLE 9

| | Stabilizer | Arg-HCl | Histidine | Lysine-HCl | Glycine |
|---|---|---|---|---|---|
| Main region [%] | Initial | 78.6 | 78.2 | 78.5 | 78.5 |
| | 40° C. after 4 weeks | 52.0 | 43.0 | 46.7 | 43.2 |
| | Main region decrease [%] | 26.6 | 35.2 | 31.8 | 35.3 |

As is apparent from Table 9, a sample added with arginine-hydrochloride showed the highest effect of suppressing components with charge heterogeneity as compared to samples added with histidine, lysine-hydrochloride, or glycine four weeks after 40° C./75% RH thermal acceleration.

INDUSTRIAL APPLICABILITY

Formulations of the present invention are formulations with excellent stability both in lyophilized state and in solution state, and characterized in that aggregate formation of proteins such as antibody molecules is suppressed after storage in solution states and after storage in lyophilized states and reconstitution by water. Formulations of the present invention in which deteriorative reaction is difficult to occur as such can be used for, for example, the treatment of atopic dermatitis and such by subcutaneous administration.

The invention claimed is:

1. A method of treating a subject affected with an IL-31-associated disorder, the method comprising administering to the subject by injection or infusion a solution formulation comprising:
- 6 to 100 mg/mL of an IL-31 antagonist that is an anti-IL-31RA antibody comprising (i) an H chain variable region that comprises a CDR1 as set forth in SEQ ID NO: 1, a CDR2 as set forth in SEQ ID NO: 2, and a CDR3 as set forth in SEQ ID NO: 3; and (ii) an L chain variable region that comprises a CDR1 as set forth in SEQ ID NO: 4, a CDR2 as set forth in SEQ ID NO: 5, and a CDR3 as set forth in SEQ ID NO: 6,
- 6 to 20 mmol/L Tris buffer,
- 45 to 150 mmol/L arginine or a salt thereof,
- 75 to 250 mmol/L sucrose or trehalose, and
- 0.15 to 0.50 mg/mL poloxamer 188 or polysorbate 20, wherein the solution formulation has a pH in the range of 6 to 8.

2. The method of claim 1, wherein the H chain variable region comprises SEQ ID NO: 7 and the L chain variable region comprises SEQ ID NO: 8.

3. The method of claim 1, wherein the anti-IL-31RA antibody comprises an H chain comprising SEQ ID NO: 9 and an L chain comprising SEQ ID NO: 10.

4. The method of claim 1, wherein the molar ratio of the arginine or salt thereof to the anti-IL-31RA antibody is in the range of 220:1 to 1100:1 and the molar ratio of the sucrose or trehalose to the anti-IL-31RA antibody is in the range of 370:1 to 1840:1.

5. The method of claim 1, wherein the molar ratio of the arginine or salt thereof to the anti-IL-31RA antibody is in the range of 220:1 to 880:1, and the molar ratio of the sucrose or trehalose to the anti-IL-31RA antibody is in the range of 370:1 to 1470:1.

6. The method of claim 1, wherein the arginine or salt thereof is arginine-hydrochloride, arginine-aspartate, or arginine-glutamate.

7. The method of claim 1, wherein the arginine or salt thereof is arginine-hydrochloride.

8. The method of claim 1, wherein the IL-31-associated disorder is an inflammatory disease involving IL-31 signaling.

9. The method of claim 1, wherein the IL-31-associated disorder is characterized by any one or more of the following symptoms in the subject: redness, induration, papules, edema, excoriations, and lichenification.

10. The method of claim 9, wherein the treatment is effective in suppressing the one or more symptoms in the subject.

11. The method of claim 1, wherein the IL-31-associated disorder is atopic dermatitis.

12. The method of claim 1, wherein the IL-31-associated disorder is dialysis-induced pruritus.

13. The method of claim 1, wherein the IL-31-associated disorder is prurigo nodularis.

14. The method of claim 1, wherein the solution formulation is subcutaneously administered to the subject.

15. A method of treating a subject affected with an IL-31-associated disorder, the method comprising:
- contacting a lyophilized formulation with water to produce a reconstituted solution; and
- administering the reconstituted solution to the subject by injection or infusion, wherein the lyophilized formulation comprises:
- an IL-31 antagonist that is an anti-IL-31RA antibody comprising (i) an H chain variable region that comprises a CDR1 as set forth in SEQ ID NO: 1, a CDR2 as set forth in SEQ ID NO: 2, and a CDR3 as set forth in SEQ ID NO: 3; and (ii) an L chain variable region that comprises a CDR1 as set forth in SEQ ID NO: 4, a CDR2 as set forth in SEQ ID NO: 5, and a CDR3 as set forth in SEQ ID NO: 6,
- Tris buffer,
- arginine or a salt thereof,
- sucrose or trehalose, and
- poloxamer 188 or polysorbate 20, wherein the molar ratio of the arginine or salt thereof to the anti-IL-31RA antibody is in the range of 220:1 to 1100:1, wherein the molar ratio of the sucrose or trehalose to the anti-IL-31RA antibody is in the range of 370:1 to 1840:1, and wherein, when the lyophilized formulation is reconstituted in water to produce a reconstituted solution, the reconstituted solution has a pH of 6 to 8.

16. The method of claim 15, wherein the molar ratio of the arginine or salt thereof to the anti-IL-31RA antibody is in the range of 220:1 to 880:1 and the molar ratio of the sucrose or trehalose to the anti-IL-31RA antibody is in the range of 370:1 to 1470:1.

17. The method of claim 15, wherein the H chain variable region comprises SEQ ID NO: 7 and the L chain variable region comprises SEQ ID NO: 8.

18. The method of claim 15, wherein the anti-IL-31RA antibody comprises an H chain comprising SEQ ID NO: 9 and an L chain comprising SEQ ID NO: 10.

19. The method of claim 15, wherein the arginine or salt thereof is arginine-hydrochloride, arginine-aspartate, or arginine-glutamate.

20. The method of claim 15, wherein the arginine or salt thereof is arginine-hydrochloride.

21. The method of claim 15, wherein the IL-31-associated disorder is an inflammatory disease involving IL-31 signaling.

22. The method of claim 15, wherein the IL-31-associated disorder is atopic dermatitis.

23. The method of claim 15, wherein the IL-31-associated disorder is dialysis-induced pruritus.

24. The method of claim 15, wherein the IL-31-associated disorder is prurigo nodularis.

25. The method of claim 15, wherein the solution formulation is subcutaneously administered to the subject.

26. The method of claim 25, wherein the volume of the solution formulation administered to the subject is 0.1 to 10 mL.

27. The method of claim 15, wherein the reconstituted solution is prepared by drawing water into a syringe that contains the lyophilized formulation.

28. The method of claim 15, wherein the lyophilized formulation is disposed in a container that is a vial, a cartridge, or a syringe, and wherein the lyophilized formulation in the container comprises:
   10 mg to 80 mg of the anti-IL-31RA antibody;
   0.8 mg to 4 mg of tris(hydroxymethyl)aminomethane;
   8 mg to 40 mg of arginine;
   30 mg to 110 mg of sucrose or trehalose; and
   0.1 mg to 0.7 mg of poloxamer 188 or polysorbate 20.

29. The method of claim 15, wherein the lyophilized formulation is a composition resulting from lyophilizing a solution comprising:
   50 mg/mL of the anti-IL-31RA antibody;
   10 mmol/L Tris-HCl;
   75 mmol/L Arg-HCl;
   125 mmol/L sucrose or trehalose; and
   0.25 mg/mL poloxamer 188 or polysorbate 20.

30. The method of claim 15, wherein the lyophilized formulation is a composition resulting from lyophilizing a solution comprising:
   7.5 mg/mL of the anti-IL-31RA antibody;
   6 mmol/L Tris-HCl;
   45 mmol/L Arg-HCl;
   75 mmol/L sucrose or trehalose; and
   0.15 mg/mL poloxamer 188 or polysorbate 20.

* * * * *

SEQUENCE LISTING

```
<160> NUMBER OF SEQ ID NOS: 12

<210> SEQ ID NO 1
<211> LENGTH: 5
<212> TYPE: PRT
<213> ORGANISM: Artificial sequence
<220> FEATURE:
<223> OTHER INFORMATION: An artificially synthesized peptide sequence

<400> SEQUENCE: 1

Gly Tyr Ile Met Asn
1               5

<210> SEQ ID NO 2
<211> LENGTH: 17
<212> TYPE: PRT
<213> ORGANISM: Artificial sequence
<220> FEATURE:
<223> OTHER INFORMATION: An artificially synthesized peptide sequence

<400> SEQUENCE: 2

Leu Ile Asn Pro Tyr Asn Gly Gly Thr Asp Tyr Asn Pro Gln Phe Gln
1               5                   10                  15

Asp

<210> SEQ ID NO 3
<211> LENGTH: 12
<212> TYPE: PRT
<213> ORGANISM: Artificial sequence
<220> FEATURE:
<223> OTHER INFORMATION: An artificially synthesized peptide sequence

<400> SEQUENCE: 3

Asp Gly Tyr Asp Asp Gly Pro Tyr Thr Leu Glu Thr
```

<210> SEQ ID NO 4
<211> LENGTH: 11
<212> TYPE: PRT
<213> ORGANISM: Artificial sequence
<220> FEATURE:
<223> OTHER INFORMATION: An artificially synthesized peptide sequence

<400> SEQUENCE: 4

Gln Ala Ser Glu Asp Ile Tyr Ser Phe Val Ala
1               5                   10

<210> SEQ ID NO 5
<211> LENGTH: 7
<212> TYPE: PRT
<213> ORGANISM: Artificial sequence
<220> FEATURE:
<223> OTHER INFORMATION: An artificially synthesized peptide sequence

<400> SEQUENCE: 5

Asn Ala Gln Thr Glu Ala Gln
1               5

<210> SEQ ID NO 6
<211> LENGTH: 9
<212> TYPE: PRT
<213> ORGANISM: Artificial sequence
<220> FEATURE:
<223> OTHER INFORMATION: An artificially synthesized peptide sequence

<400> SEQUENCE: 6

Gln His His Tyr Asp Ser Pro Leu Thr
1               5

<210> SEQ ID NO 7
<211> LENGTH: 121
<212> TYPE: PRT
<213> ORGANISM: Artificial sequence
<220> FEATURE:
<223> OTHER INFORMATION: An artificially synthesized peptide sequence

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Ile Met Asn Trp Val Arg Gln Ala Pro Gly Gln Gly Leu Glu Trp Met
            35                  40                  45

Gly Leu Ile Asn Pro Tyr Asn Gly Gly Thr Asp Tyr Asn Pro Gln Phe
        50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
                100                 105                 110

Gln Gly Thr Leu Val Thr Val Ser Ser
            115                 120

<210> SEQ ID NO 8
<211> LENGTH: 107
<212> TYPE: PRT

<213> ORGANISM: Artificial sequence
<220> FEATURE:
<223> OTHER INFORMATION: An artificially synthesized peptide sequence

<400> SEQUENCE: 8

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Phe
            20                  25                  30

Val Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Asp Ser Pro Leu
                85                  90                  95

Thr Phe Gly Gly Gly Thr Lys Val Glu Ile Lys
            100                 105
```

<210> SEQ ID NO 9
<211> LENGTH: 445
<212> TYPE: PRT
<213> ORGANISM: Artificial sequence
<220> FEATURE:
<223> OTHER INFORMATION: An artificially synthesized peptide sequence

<400> SEQUENCE: 9

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220
```

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
            325                 330                 335

Ser Lys Thr Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Pro
    435                 440                 445

<210> SEQ ID NO 10
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Phe
            20                  25                  30

Val Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Ser Pro Leu
            85                  90                  95

Thr Phe Gly Gly Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 11
<211> LENGTH: 764
<212> TYPE: PRT
<213> ORGANISM: Homo sapiens

<400> SEQUENCE: 11

```
Met Cys Ile Arg Gln Leu Lys Phe Phe Thr Thr Ala Cys Val Cys Glu
1               5                   10                  15

Cys Pro Gln Asn Ile Leu Ser Pro Gln Pro Ser Cys Val Asn Leu Gly
                20                  25                  30

Met Met Trp Thr Trp Ala Leu Trp Met Leu Pro Ser Leu Cys Lys Phe
            35                  40                  45

Ser Leu Ala Ala Leu Pro Ala Lys Pro Glu Asn Ile Ser Cys Val Tyr
50                  55                  60

Tyr Tyr Arg Lys Asn Leu Thr Cys Thr Trp Ser Pro Gly Lys Glu Thr
65                  70                  75                  80

Ser Tyr Thr Gln Tyr Thr Val Lys Arg Thr Tyr Ala Phe Gly Glu Lys
                85                  90                  95

His Asp Asn Cys Thr Thr Asn Ser Ser Thr Ser Glu Asn Arg Ala Ser
                100                 105                 110

Cys Ser Phe Phe Leu Pro Arg Ile Thr Ile Pro Asp Asn Tyr Thr Ile
            115                 120                 125

Glu Val Glu Ala Glu Asn Gly Asp Gly Val Ile Lys Ser His Met Thr
130                 135                 140

Tyr Trp Arg Leu Glu Asn Ile Ala Lys Thr Glu Pro Pro Lys Ile Phe
145                 150                 155                 160

Arg Val Lys Pro Val Leu Gly Ile Lys Arg Met Ile Gln Ile Glu Trp
                165                 170                 175

Ile Lys Pro Glu Leu Ala Pro Val Ser Ser Asp Leu Lys Tyr Thr Leu
            180                 185                 190

Arg Phe Arg Thr Val Asn Ser Thr Ser Trp Met Glu Val Asn Phe Ala
        195                 200                 205

Lys Asn Arg Lys Asp Lys Asn Gln Thr Tyr Asn Leu Thr Gly Leu Gln
210                 215                 220

Pro Phe Thr Glu Tyr Val Ile Ala Leu Arg Cys Ala Val Lys Glu Ser
225                 230                 235                 240

Lys Phe Trp Ser Asp Trp Ser Gln Glu Lys Met Gly Met Thr Glu Glu
                245                 250                 255

Glu Ala Pro Cys Gly Leu Glu Leu Trp Arg Val Leu Lys Pro Ala Glu
            260                 265                 270

Ala Asp Gly Arg Arg Pro Val Arg Leu Leu Trp Lys Lys Ala Arg Gly
        275                 280                 285

Ala Pro Val Leu Glu Lys Thr Leu Gly Tyr Asn Ile Trp Tyr Tyr Pro
290                 295                 300
```

```
Glu Ser Asn Thr Asn Leu Thr Glu Thr Met Asn Thr Asn Gln Gln
305                 310                 315                 320

Leu Glu Leu His Leu Gly Gly Glu Ser Phe Trp Val Ser Met Ile Ser
                325                 330                 335

Tyr Asn Ser Leu Gly Lys Ser Pro Val Ala Thr Leu Arg Ile Pro Ala
            340                 345                 350

Ile Gln Glu Lys Ser Phe Gln Cys Ile Glu Val Met Gln Ala Cys Val
        355                 360                 365

Ala Glu Asp Gln Leu Val Val Lys Trp Gln Ser Ser Ala Leu Asp Val
    370                 375                 380

Asn Thr Trp Met Ile Glu Trp Phe Pro Asp Val Asp Ser Glu Pro Thr
385                 390                 395                 400

Thr Leu Ser Trp Glu Ser Val Ser Gln Ala Thr Asn Trp Thr Ile Gln
                405                 410                 415

Gln Asp Lys Leu Lys Pro Phe Trp Cys Tyr Asn Ile Ser Val Tyr Pro
            420                 425                 430

Met Leu His Asp Lys Val Gly Glu Pro Tyr Ser Ile Gln Ala Tyr Ala
        435                 440                 445

Lys Glu Gly Val Pro Ser Glu Gly Pro Glu Thr Lys Val Glu Asn Ile
    450                 455                 460

Gly Val Lys Thr Val Thr Ile Thr Trp Lys Glu Ile Pro Lys Ser Glu
465                 470                 475                 480

Arg Lys Gly Ile Ile Cys Asn Tyr Thr Ile Phe Tyr Gln Ala Glu Gly
                485                 490                 495

Gly Lys Gly Phe Ser Lys Thr Val Asn Ser Ser Ile Leu Gln Tyr Gly
            500                 505                 510

Leu Glu Ser Leu Lys Arg Lys Thr Ser Tyr Ile Val Gln Val Met Ala
        515                 520                 525

Ser Thr Ser Ala Gly Gly Thr Asn Gly Thr Ser Ile Asn Phe Lys Thr
    530                 535                 540

Leu Ser Phe Ser Val Phe Glu Ile Ile Leu Ile Thr Ser Leu Ile Gly
545                 550                 555                 560

Gly Gly Leu Leu Ile Leu Ile Ile Leu Thr Val Ala Tyr Gly Leu Lys
                565                 570                 575

Lys Pro Asn Lys Leu Thr His Leu Cys Trp Pro Thr Val Pro Asn Pro
            580                 585                 590

Ala Glu Ser Ser Ile Ala Thr Trp His Gly Asp Asp Phe Lys Asp Lys
        595                 600                 605

Leu Asn Leu Lys Glu Ser Asp Ser Val Asn Thr Glu Asp Arg Ile
    610                 615                 620

Leu Lys Pro Cys Ser Thr Pro Ser Asp Lys Leu Val Ile Asp Lys Leu
625                 630                 635                 640

Val Val Asn Phe Gly Asn Val Leu Gln Glu Ile Phe Thr Asp Glu Ala
                645                 650                 655

Arg Thr Gly Gln Glu Asn Asn Leu Gly Gly Glu Lys Asn Gly Tyr Val
            660                 665                 670

Thr Cys Pro Phe Arg Pro Asp Cys Pro Leu Gly Lys Ser Phe Glu Glu
        675                 680                 685

Leu Pro Val Ser Pro Glu Ile Pro Pro Arg Lys Ser Gln Tyr Leu Arg
    690                 695                 700

Ser Arg Met Pro Glu Gly Thr Arg Pro Glu Ala Lys Glu Gln Leu Leu
705                 710                 715                 720
```

Phe Ser Gly Gln Ser Leu Val Pro Asp His Leu Cys Glu Glu Gly Ala
                725                 730                 735

Pro Asn Pro Tyr Leu Lys Asn Ser Val Thr Ala Arg Glu Phe Leu Val
            740                 745                 750

Ser Glu Lys Leu Pro Glu His Thr Lys Gly Glu Val
        755                 760

<210> SEQ ID NO 12
<211> LENGTH: 326
<212> TYPE: PRT
<213> ORGANISM: Homo sapiens

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

```
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
                325
```